United States Patent
Cao et al.

(10) Patent No.: US 12,146,133 B2
(45) Date of Patent: Nov. 19, 2024

(54) BIOTIN-STREPTAVIDIN CLEAVAGE COMPOSITION AND LIBRARY FRAGMENT CLEAVAGE

(71) Applicant: ILLUMINA, INC., San Diego, CA (US)

(72) Inventors: Dan Cao, East Palo Alto, CA (US); Jeffrey S. Fisher, San Diego, CA (US); Fiona Kaper, Solana Beach, CA (US); Tarun Kumar Khurana, Fremont, CA (US); Tong Liu, Belmont, CA (US); Burak Okumus, San Diego, CA (US); Victor J. Quijano, Mountain View, CA (US); Clifford Lee Wang, Berkeley, CA (US); Yir-Shyuan Wu, Albany, CA (US); Shi Min Xiao, Castro Valley, CA (US); Hongxia Xu, Castro Valley, CA (US)

(73) Assignee: Illumina, Inc., San Diego, CA (US)

( * ) Notice: Subject to any disclaimer, the term of this patent is extended or adjusted under 35 U.S.C. 154(b) by 768 days.

(21) Appl. No.: 17/166,906

(22) Filed: Feb. 3, 2021

(65) Prior Publication Data

US 2021/0238589 A1    Aug. 5, 2021

Related U.S. Application Data

(63) Continuation of application No. PCT/US2021/016228, filed on Feb. 2, 2021.

(51) Int. Cl.
*C12N 15/10* (2006.01)

(52) U.S. Cl.
CPC .............................. *C12N 15/1068* (2013.01)

(58) Field of Classification Search
None
See application file for complete search history.

(56) References Cited

U.S. PATENT DOCUMENTS

| | | |
|---|---|---|
| 2013/0017978 A1 | 1/2013 | Kavanagh et al. |
| 2017/0283864 A1 | 10/2017 | Ach et al. |

FOREIGN PATENT DOCUMENTS

| | | |
|---|---|---|
| CN | 101622340 A | 1/2010 |
| CN | 102369295 A | 3/2012 |
| CN | 103298949 A | 9/2013 |
| CN | 103597097 A | 2/2014 |
| CN | 108779490 A | 11/2018 |
| EP | 0456304 A1 | 11/1991 |
| EP | 2479268 A1 | 7/2012 |
| JP | 2005336107 A | 12/2005 |
| WO | 9743617 A2 | 11/1997 |
| WO | 2011143231 A2 | 11/2011 |
| WO | 2019089836 A1 | 5/2019 |

OTHER PUBLICATIONS

Knoglinger et al. "Regenerative Biosensor for Use with Biotinylated Bait Molecules", Biosensors and Bioelectronics, vol. 99, pp. 684-690, publishes Jan. 15, 2018. (Year: 2018).*

* cited by examiner

*Primary Examiner* — Nancy J Leith
*Assistant Examiner* — Jessica D Parisi
(74) *Attorney, Agent, or Firm* — Dierker & Kavanaugh, P.C.

(57) ABSTRACT

An example of a biotin-streptavidin cleavage composition includes a formamide reagent and a salt buffer. The formamide reagent is present in the biotin-streptavidin cleavage composition in an amount ranging from about 10% to about 50%, based on a total volume of the biotin-streptavidin cleavage composition. The salt buffer makes up the balance of the biotin-streptavidin cleavage composition. In some examples, the biotin-streptavidin cleavage composition is used to cleave library fragments from a solid support. In other examples, other mechanisms are used to cleave library fragments from a solid support.

11 Claims, 8 Drawing Sheets

BIOTIN-STREPTAVIDIN CLEAVAGE COMPOSITION AND LIBRARY FRAGMENT CLEAVAGE

CROSS-REFERENCE TO RELATED APPLICATIONS

This application is a continuation of International Application Number PCT/US2021/016228, filed Feb. 2, 2021, which itself claims the benefit of U.S. Provisional Application Ser. No. 62/969,440, filed Feb. 3, 2020, the contents of which is incorporated by reference herein in its entirety.

BACKGROUND

Biological arrays are among a wide range of tools used to detect, analyze, and/or purify molecules, including proteins, nucleic acids, etc. In some applications, the arrays are engineered to include probes that can capture the molecule of interest. In other applications, the arrays are engineered with one member of a binding pair, and the molecule of interest is labeled or tagged with the other member of the binding pair. Examples of binding pairs include biotin and avidin or streptavidin. The affinity of avidin or streptavidin for biotin is one of the strongest non-covalent biological interactions. Moreover, a biotin label rarely interferes with the function of the labeled molecule. These properties render biotin and avidin or biotin and streptavidin particularly desirable for a variety of biological applications.

In some biological applications, it is desirable for molecules of interest to be tethered or linked in a conditional and controlled manner, where the tether or linkage is cleaved at a particular time and the dissociation of the cleaved molecule interest is controlled. In some instances, the strength of the biotin and avidin or biotin and streptavidin interaction may render conditional and/or controlled cleavage difficult.

SUMMARY

Disclosed herein are compositions and methods that may be used to cleave library fragments from a solid support to which they are attached. One example composition is capable of quickly and effectively cleaving biotin-streptavidin bonds. Another example composition is activated under conditions that allow for spatial release of the library fragments. One example method involves a two-step release of the library fragments from the solid support. The cleavage mechanisms in the two-step release are orthogonal, and thus the first cleavage mechanism is labile while second cleavage mechanism is stable. The second cleavage mechanism allows for spatial release of the library fragments.

The compositions and methods may be used on a flow cell. Each of the examples disclosed herein can be used on the flow cell surface without deleteriously affect the chemistry e.g., polymeric hydrogel, amplification primers, etc.) on the flow cell surface.

A first aspect disclosed herein is a biotin-streptavidin cleavage composition, comprising: from about 10% by volume to about 50% by volume of a formamide reagent; and a balance of a salt buffer.

A second aspect disclosed herein in a biotin-streptavidin cleavage composition, consisting of: from about 10% by volume to about 50% by volume of a formamide reagent including formamide and an optional buffer; and a balance of a salt buffer including sodium chloride, sodium citrate, and a biocompatible surfactant.

A third aspect disclosed herein is a method, comprising: introducing library fragments to a flow cell, wherein the library fragments are attached to streptavidin coated solid supports; introducing a biotin-streptavidin cleavage composition to the flow cell, the biotin-streptavidin cleavage composition including from about 10% by volume to about 50% by volume of a formamide reagent and a balance of a salt buffer; and allowing the biotin-streptavidin cleavage composition to incubate in the flow cell at a temperature ranging from about 60° C. to about 70° C., thereby causing at least some of the library fragments to release from the solid supports and to seed to amplification primers on a surface of the flow cell.

A fourth aspect disclosed herein is a kit, comprising: a streptavidin coated solid support; an adapter sequence having biotin attached at one end, wherein the biotin is to be attached to the streptavidin coated solid support; a sample fluid including a genomic sequence that is to be fragmented and attached to the adapter sequence; and a biotin-streptavidin cleavage composition, including from about 10% by volume to about 50% by volume of a formamide reagent and a balance of a salt buffer.

A fifth aspect disclosed herein is a method comprising introducing desthiobiotinylated library fragments to a flow cell, wherein the desthiobiotinylated library fragments are attached to streptavidin coated solid supports; introducing a cleavage composition to the flow cell, wherein the cleavage composition is at a temperature ranging from about 18° C. to about 30° C. and wherein the cleavage composition includes free biotin and a salt buffer; and increasing the temperature of the cleavage composition to about 60° C. to about 70° C., thereby causing at least some of the library fragments to release from the solid supports and to seed to amplification primers on a surface of the flow cell.

A sixth aspect disclosed herein is a library preparation fluid comprising a liquid carrier and library preparation beads in the liquid carrier; each library preparation bead including a solid support and a transposome complex attached to the solid support; the transposome complex including a transposase enzyme, a double stranded molecule bound to the transposase enzyme, the double stranded molecule including: a transferred strand including a 3' transposon end sequence, an adapter sequence, a cleavage site, and a 5' linking end sequence, wherein the adapter sequence and the 5' linking end sequence flank the cleavage site, and a non-transferred strand including a 3' transposon end sequence; and a splint sequence hybridized to at least a portion of the adapter sequence and at least a portion of the 5' linking end sequence such that it splints the cleavage site.

A seventh aspect disclosed herein is a method comprising introducing a plurality of prepped library preparation beads to a reaction vessel, each of the prepped library preparation beads including a solid support; a plurality of bridged molecules attached to the solid support, each of the bridged molecules including a double stranded DNA fragment, a transferred strand respectively attached to each strand of the double stranded DNA fragment at its 5' end, each transferred strand including a 3' transposon end sequence, a first adapter sequence, a cleavage site, and a 5' linking end sequence, wherein the first adapter sequence and the 5' linking end sequence flank the cleavage site, and a second adapter sequence respectively attached to each strand of the double stranded DNA fragment at its 3' end; and a splint sequence 68 hybridized to at least a portion of the first adapter sequence and at least a portion of the 5' linking end sequence such that it splints the cleavage site; exposing the prepped library preparation beads to a cleaving agent to remove the cleavage site, whereby the plurality of bridged molecules remains attached to the solid support through the splint; and heating the reaction vessel to a dissociation temperature of the splint and the double stranded DNA fragment.

It is to be understood that any features of any one of the aspects may be combined together in any desirable manner. Moreover, it is to be understood that any combination of features of the first aspect and/or of the second aspect and/or of the third aspect and/or of the fourth aspect and/or of the fifth aspect and/or of the sixth aspect and/or of the seventh aspect may be combined with any of the examples disclosed herein to achieve the benefits as described in this disclosure, including, for example, improved biotin-streptavidin bond cleavage.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1A:
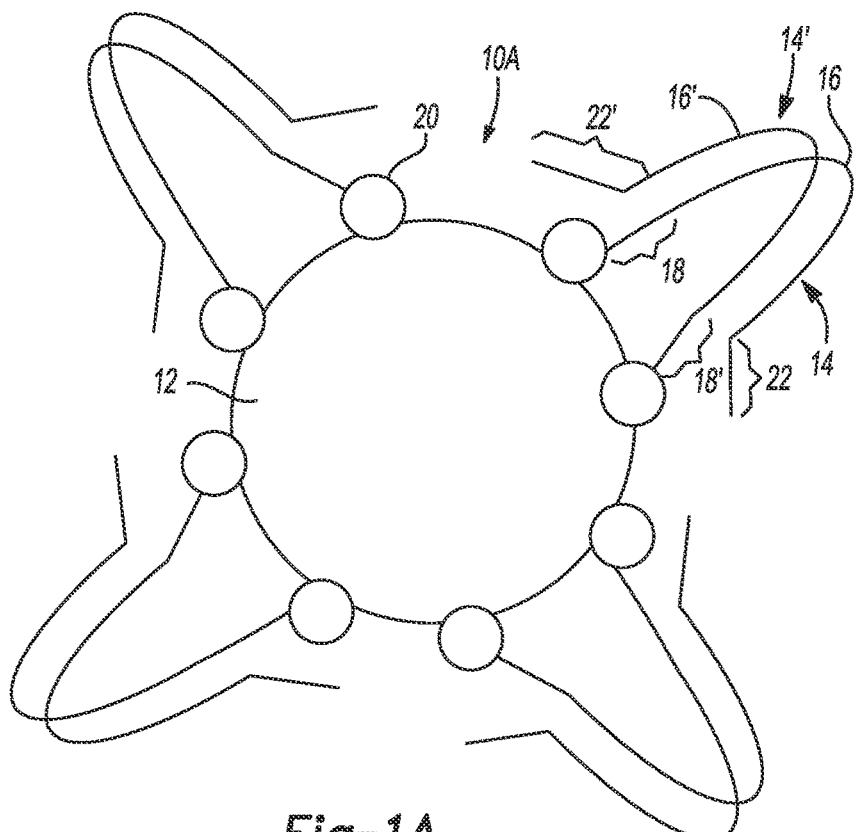
FIGS. 1A and 1B are schematic illustrations of different examples of the target materials disclosed herein.

In some sequencing applications, DNA library fragments are introduced to a flow cell on a solid support (e.g., a bead). The use of the solid support may be desirable because it can preserve the contiguity information of the longer genetic material from which the library fragments are generated. In some instances, the DNA library fragments are attached to the solid support using biotin-streptavidin interaction. For library seeding and amplification on the flow cell, the biotinylated DNA library fragments have to be released from the solid support. The present inventors have found that some reagents that are strong enough to break the biotin-streptavidin interaction also interfere with or otherwise deleteriously affect the hybridization of the biotinylated DNA library fragments to primers on the flow cell surface. As one example, a strong denaturing reagent (e.g., about 95% formamide and about 10 mM ethylenediaminetetraacetic acid (EDTA)) and a high temperature incubation (e.g., 2 minutes at 90° C.) has been found to break the biotin-streptavidin interaction, however, the released biotinylated DNA library fragments do not hybridize to the flow cell surface.

In one example, a cleavage composition is disclosed herein that is capable of efficiently breaking the biotin-streptavidin bonds, which fully releases the biotinylated DNA library fragments. Upon being released and within the cleavage composition, the biotinylated DNA library fragments are able to undergo hybridization. As such, the cleavage composition disclosed herein efficiently breaks the biotin-streptavidin interaction and ensures immediate hybridization. The cleavage composition is also effective at temperatures equal to or less than 70° C. 70° C. is below the operating temperature of most flow cells, and thus the use of the cleavage composition in the flow cell does not deleteriously affect the chemistry e.g., polymeric hydrogel, amplification primers, etc.) on the flow cell surface.

The cleavage composition disclosed herein can also effectively break the biotin-streptavidin bonds very quickly. In some instances, the incubation time ranges from about 2 minutes to about 5 minutes. These times are significantly reduced when compared to other methods, e.g., those involving sodium dodecyl sulfate (SDS), urea and biotin, which may involve 15 minutes of shaking and 15 minutes of incubation.

The cleavage composition disclosed herein may also be used in other applications where it is desirable to break the binding pair of biotin-streptavidin.

In another example, the biotinylated DNA library fragments are replaced with desthiobiotinylated DNA library fragments. In this example, the cleavage is activated under conditions that allow for spatial release of the library fragments. By "spatial release," it is meant that the DNA fragments are released in the absence of inertial fluid mixing and thus can controllably diffuse and seed on the flow cell surface within proximity of the solid support from which the fragments were released. When cleavage occurs on a flow cell surface, the cleavage conditions do not deleteriously affect the chemistry e.g., polymeric hydrogel, amplification primers, etc.) on the flow cell surface.

In still another example, the DNA library fragments are attached to the solid support with a dual release mechanism. The dual release mechanism includes a cleavage site and a splint; both of which hold the library fragment to the solid support, and each of which involves a different release process. When library fragment release is desired, a suitable cleaving agent may be used to first remove the cleavage site, and then heat may be used to remove the splint. Because the cleavage conditions involve two orthogonal processes (where one process does not initiate, affect, or otherwise interfere with the other process), this example allows for controlled release of the library fragments.

Definitions

Terms used herein will be understood to take on their ordinary meaning in the relevant art unless specified otherwise. Several terms used herein and their meanings are set forth below.

As used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, non-recited elements or method steps.

Reference throughout the specification to "one example," "another example," "an example," and so forth, means that a particular element (e.g., feature, structure, composition, configuration, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, these terms can refer to less than or equal to ±10% from a stated value, such as less than or equal to ±5% from a stated value, such as less than or equal to ±2% from a stated value, such as less than or equal to ±1% from a stated value, such as less than or equal to ±0.5% from a stated value, such as less than or equal to ±0.2% from a stated value, such as less than or equal to ±0.1% from a stated value, such as less than or equal to ±0.05% from a stated value.

Furthermore, it is to be understood that the ranges provided herein include the stated range and any value or sub-range within the stated range, as if they were explicitly recited. For example, a range represented by from about 2 mm to about 300 mm, should be interpreted to include not only the explicitly recited limits of from about 2 mm to about 300 mm, but also to include individual values, such as about 15 mm, 22.5 mm, 245 mm, etc., and sub-ranges, such as from about 20 mm to about 225 mm, etc.

Adapter: A linear oligonucleotide sequence that can be fused to a nucleic acid molecule, for example, by ligation or tagmentation. Suitable adapter lengths may range from about 10 nucleotides to about 100 nucleotides, or from about 12 nucleotides to about 60 nucleotides, or from about 15 nucleotides to about 50 nucleotides. The adapter may include any combination of nucleotides and/or nucleic acids. In some examples, the adapter can include a sequence that is complementary to at least a portion of a primer, for example, a primer including a universal nucleotide sequence (such as a P5 or P7 sequence). As one specific example, the adapter at one end of a fragment includes a sequence that is complementary to at least a portion of a first flow cell primer, and the adapter at the other end of the fragment includes a sequence that is identical to at least a portion of a second flow cell primer. The complementary adapter can hybridize to the first flow cell primer, and the identical adapter is a template for its complementary copy, which can hybridize to the second flow cell primer during clustering. In some examples, the adapter can include a sequencing primer sequence or sequencing binding site. Combinations of different adapters may be incorporated into a nucleic acid molecule, such as a DNA fragment.

Chemical Capture site: A portion of a flow cell surface having been modified with a chemical property that allows for localization of a target material (e.g., complexes, protein biomarkers, etc.). In an example, the capture site may include a chemical capture agent (i.e., a material, molecule or moiety that is capable of attaching, retaining, or binding to a target molecule (e.g., a complex)). One example chemical capture agent includes a member of a receptor-ligand binding pair (e.g., avidin, streptavidin, biotin, lectin, carbohydrate, nucleic acid binding protein, epitope, antibody, etc.) that is capable of binding to the target material (or to a linking moiety attached to the target material). Yet another example of the chemical capture agent is a chemical reagent capable of forming an electrostatic interaction, a hydrogen bond, or a covalent bond (e.g., thiol-disulfide exchange, click chemistry, Diels-Alder, etc.) with the target material.

Complex: A carrier, such as a solid support, and sequencing-ready nucleic acid fragments attached to the carrier. In some of the examples disclosed herein, the carrier also includes one member of a biotin-streptavidin binding pair whose other member is part of the capture site.

Depositing: Any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

Depression: A discrete concave feature in a substrate or a patterned resin having a surface opening that is at least partially surrounded by interstitial region(s) of the substrate or the patterned resin. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

Desthiobiotin: A sulfur free biotin analogue that binds less tightly to avidin and streptavidin than biotin. The term may also include dual desthiobiotin and triple desthiobiotin.

Each: When used in reference to a collection of items, each identifies an individual item in the collection, but does not necessarily refer to every item in the collection. Exceptions can occur if explicit disclosure or context clearly dictates otherwise.

Flow Cell: A vessel having a chamber (e.g., which may include a flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber can include one or more transparent surfaces allowing for the optical detection of arrays, optically labeled molecules, or the like.

Flow channel: An area defined between two bonded or otherwise attached components, which can selectively receive a liquid sample. In some examples, the flow channel may be defined between two patterned or non-patterned sequencing surfaces, and thus may be in fluid communication with one or more components of the sequencing surfaces.

Fragment: A portion or piece of genetic material (e.g., DNA, RNA, etc.). Contiguity preserved library fragments are smaller pieces of the longer nucleic acid sample that has been fragmented, where the contiguity information of the longer nucleic acid sample has been preserved in the fragments.

Nucleic acid molecule or sample: A polymeric form of nucleotides of any length, and may include ribonucleotides, deoxyribonucleotides, analogs thereof, or mixtures thereof. The term may refer to single stranded or double stranded polynucleotides.

A "template" nucleic acid molecule (or strand) may refer to a sequence that is to be analyzed.

The nucleotides in a nucleic acid sample may include naturally occurring nucleic acids and functional analogs thereof. Examples of functional analogs are capable of hybridizing to a nucleic acid in a sequence specific fashion or capable of being used as a template for replication of a particular nucleotide sequence. Naturally occurring nucleotides generally have a backbone containing phosphodiester bonds. An analog structure can have an alternate backbone linkage including any of a variety known in the art. Naturally occurring nucleotides generally have a deoxyribose sugar (e.g., found in DNA) or a ribose sugar (e.g., found in RNA). An analog structure can have an alternate sugar moiety including any of a variety known in the art. Nucleotides can include native or non-native bases. A native DNA can include one or more of adenine, thymine, cytosine and/or guanine, and a native RNA can include one or more of adenine, uracil, cytosine and/or guanine. Any non-native base may be used, such as a locked nucleic acid (LNA) and a bridged nucleic acid (BNA).

Primer: A nucleic acid molecule that can hybridize to a target sequence, such as an adapter attached to a library fragment. As one example, an amplification primer can serve as a starting point for template amplification and cluster generation. As another example, a synthesized nucleic acid (template) strand may include a site to which a primer (e.g., a sequencing primer) can hybridize in order to prime synthesis of a new strand that is complementary to the synthesized nucleic acid strand. Any primer can include any combination of nucleotides or analogs thereof. In some examples, the primer is a single-stranded oligonucleotide or polynucleotide. The primer length can be any number of bases long and can include a variety of non-natural nucleotides. In an example, the sequencing primer is a short strand, ranging from 10 to 60 bases, or from 20 to 40 bases.

Sequencing-ready nucleic acid fragments: A portion of genetic material having adapters at the 3' and 5' ends. In the sequencing-ready nucleic acid fragment, each adapter includes a known universal sequence (e.g., which is complementary to or identical to at least a portion of a primer on a flow cell) and a sequencing primer sequence. Both of the adapters may also include an index (barcode or tag) sequence. In an example, one side (e.g., including a P5' or P5 sequence) may contain a solid support index and the other side (including a P7 or P7' sequence) may contain a sample index. A sequencing-ready nucleic acid fragment may be bound via insertion of transposons, where inserted DNA molecules are immobilized to the surface of a solid support (e.g., bead); or directly immobilized through a binding pair or other cleavable linker; or bound via hybridization, where complementary adapter sequences are present on the surface of the solid support.

Sequencing surface: A polymeric hydrogel having one or more types of amplification primers grafted thereto. The sequencing surface may also include a chemical capture agent to immobilize complexes at or near the amplification primers.

Solid support: A small body made of a rigid or semi-rigid material having a shape characterized, for example, as a sphere, oval, microsphere, or other recognized particle shape whether having regular or irregular dimensions. The solid support can have a sequencing library attached thereto.

Target Material: Any substance that includes a biotin-streptavidin bond or a desthiobiotin-streptavidin bond.

Transferred and Non-Transferred Strands: The term "transferred strand" refers to a sequence that includes a transferred portion of two hybridized transposon ends. Similarly, the term "non-transferred strand" refers to a sequence that includes the non-transferred portion of two hybridized transposon ends. The 3'-end of a transferred strand is joined or transferred to a double stranded fragment in an in vitro transposition reaction. The non-transferred strand, which exhibits a transposon end sequence that is complementary to the transferred transposon end sequence, is not joined or transferred to the double stranded fragment in the in vitro transposition reaction.

Transposase: An enzyme that is capable of forming a functional complex with a transposon end-containing composition (e.g., transposons, transposon ends, transposon end compositions) and catalyzing insertion or transposition of the transposon end-containing composition into the double-stranded DNA sample with which it is incubated, for example, in an in vitro transposition reaction. A transposase as presented herein can also include integrases from retrotransposons and retroviruses. Although many examples described herein refer to Tn5 transposase and/or hyperactive Tn5 transposase, it will be appreciated that any transposition system that is capable of inserting a transposon end with sufficient efficiency to 5'-tag and fragment the DNA sample for its intended purpose can be used. In particular examples, the transposition system is capable of inserting the transposon end in a random or in an almost random manner to 5'-tag and fragment the DNA sample.

Transposome Complex: A complex formed between an integration enzyme (e.g., an integrase or a transposase) and a nucleic acid including an integration recognition site (e.g., a transposase recognition site). For example, the transposome complex can be a transposase enzyme pre-incubated with double-stranded transposon DNA under conditions that support non-covalent complex formation. Double-stranded transposon DNA can include, for example, Tn5 DNA, a portion of Tn5 DNA, a transposon end composition, a mixture of transposon end compositions or other double-stranded DNAs capable of interacting with a transposase, such as the hyperactive Tn5 transposase.

Transposon End: A double-stranded nucleic acid DNA that exhibits only the nucleotide sequences (the "transposon end sequences") that are necessary to form the complex with a transposase or integrase enzyme that is functional in an in vitro transposition reaction. In some examples, a transposon end is capable of forming a functional complex with the transposase in a transposition reaction. As examples, transposon ends can include the 19-base pair (bp) outer end ("OE") transposon end, the inner end ("IE") transposon end, or the "mosaic end" ("ME") transposon end recognized by a wild-type or mutant Tn5 transposase. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can comprise nicks in one or both strands. Although the term "DNA" may be used throughout the present disclosure in connection with the composition of transposon ends, it should be understood that any suitable nucleic acid or nucleic acid analogue can be utilized in a transposon end.

Cleavage Compositions

A first example of the cleavage composition disclosed herein is suitable for breaking biotin-streptavidin interactions at temperatures equal to or less than 70° C.

The first example of the cleavage composition includes from about 10% by volume to about 50% by volume of a formamide reagent; and a balance of a salt buffer.

The formamide reagent includes formamide:

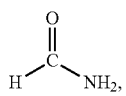

which is also known as methanamide. In some examples, the formamide reagent may include formamide alone (without any other components). As such, in some examples, the formamide reagent is 100% formamide. In other examples, the formamide reagent may include formamide and an optional buffer.

The balance of the first example of the cleavage composition is a salt buffer. Any suitable salt buffer may be used. As examples, the salt buffer is an aqueous solution including sodium chloride, sodium citrate, or combinations thereof. In one specific example, the salt buffer includes about 0.75 M (750 mM) sodium chloride and about 75 mM sodium citrate in water. In some examples, the salt buffer includes water with from about 0.5 M sodium chloride to about 3 M sodium chloride and/or from about 50 mM sodium citrate to about 300 mM sodium citrate.

The salt buffer may also include a biocompatible surfactant. An example of a suitable biocompatible surfactant is polyethylene glycol sorbitan monolaurate or polysorbate 20 (commercially available as TWEEN™ 20 sold by Sigma-Aldrich). In some examples, the salt buffer further includes from about 0.25 wt % to about 1.5 wt % of the biocompatible surfactant (based on the total weight of the salt buffer).

The first example of the cleavage composition includes from about 10% by volume to about 50% by volume of the formamide reagent and a balance of the salt buffer. As such, the amount of the salt buffer (and its individual components) in the first example of the cleavage composition depends upon the amount of the formamide reagent that is present. As examples, the first example of the cleavage composition may include about 10% by volume of the formamide reagent and about 90% by volume of the salt buffer; or about 20% by volume of the formamide reagent and about 80% by volume of the salt buffer; or about 30% by volume of the formamide reagent and about 70% by volume of the salt buffer; or about 40% by volume of the formamide reagent and about 60% by volume of the salt buffer; or about 50% by volume of the formamide reagent and about 50% by volume of the salt buffer. When higher amounts (over 50%) of the formamide reagent are included, released library fragments that have hybridized to amplification primers may denature at 25° C., which is undesirable.

In some examples, the first example of the cleavage composition consists of from about 10% by volume to about 50% by volume of a formamide reagent including formamide and an optional buffer and a balance of a salt buffer including sodium chloride, sodium citrate, and a biocompatible surfactant. In this example, the first example of the cleavage composition does not include any other components.

A second example of the cleavage composition disclosed herein is suitable for breaking desthiobiotin-streptavidin interactions at temperatures ranging from about 60° C. to about 70° C.

The second example of the cleavage composition includes free biotin and a salt buffer.

The amount of free biotin in the second example of the cleavage composition depends, in part, upon the amount of desthiobiotin-streptavidin interactions that are to be broken with the cleavage composition. In one example, the free biotin may be present in an amount ranging from about 10 moles to about 100 moles higher than the amount of desthiobiotin-streptavidin interactions to be broken. As one specific example, the free biotin is present in the second example of the cleavage composition at a concentration ranging from about 2.5 µM to about 10 mM. In another example, the free biotin is present in the second example of the cleavage composition at a concentration ranging from about 4 µM to about 8 mM.

The balance of the second example of the cleavage composition is a salt buffer. Any suitable aqueous solution including a salt may be used. In some examples, the salt is sodium chloride, sodium citrate, or combinations thereof. The salt buffer has a relatively high salt concentration. For example, the salt buffer includes from about 0.75 M salt to about 0.85 M salt in water. In one specific example, the salt buffer includes about 0.75 M (750 mM) sodium chloride and about 75 mM sodium citrate in water.

The salt buffer may also include a biocompatible surfactant. Examples of a suitable biocompatible surfactant include polyethylene glycol sorbitan monolaurate or polysorbate 20 (commercially available as TWEEN™ 20 sold by Sigma-Aldrich). In some examples, the salt buffer further includes from about 0.1 wt % to about 1 wt % of the biocompatible surfactant.

In some examples, the second example of the cleavage composition consists of the free biotin and a balance of the salt buffer including sodium chloride, sodium citrate, and a biocompatible surfactant. In this example, the second example of the cleavage composition does not include any other components.

Target Materials Including Biotin-Streptavidin Bonds or Desthiobiotin-Streptavidin Bonds In some examples disclosed herein, the first cleavage composition may be used with any target material including a biotin-streptavidin bond that is to be broken. In other examples disclosed herein, the second cleavage composition may be used with any target material including a desthiobiotin-streptavidin bond that is to be broken. In any of these examples, the target material may be a complex.

Figure 1B:
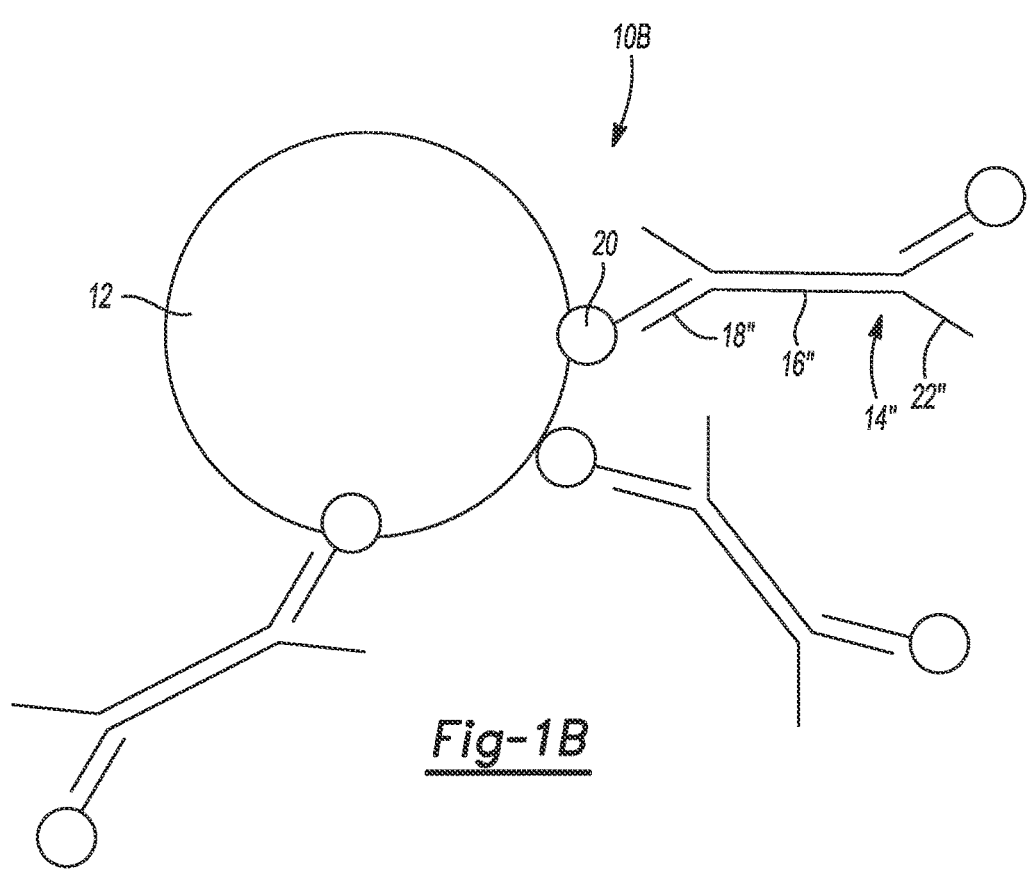

Some example complexes 10A and 10B are shown, respectively, in FIG. 1A and FIG. 1B. In some examples of the method disclosed herein, the complexes 10A, 10B include a solid support 12 and DNA library fragments 14, 14', 14" attached to the solid support 12 through biotin-streptavidin bonds. In other examples of the method disclosed herein, the complexes 10A, 10B include a solid support 12 and DNA library fragments 14, 14', 14" attached to the solid support 12 through desthiobiotin-streptavidin bonds.

The solid support 12 may be, without limitation, glass (e.g., controlled pore glass beads); magnetically responsive materials; plastic, such as acrylic, polystyrene or a copolymer of styrene and another material, polypropylene, polyethylene, polybutylene, polyurethane or polytetrafluoroethylene (TEFLON® from The Chemours Co); polysaccharides or cross-linked polysaccharides such as agarose SEPHAROSE® beads (cross-linked beaded form of agarose, available from Cytivia), or SEPHADEX® beads (cross-linked beaded form of dextran, available from Cytivia); nylon; nitrocellulose; resin; silica or silica-based materials including silicon and modified silicon; carbon-fiber; metal; inorganic glass; an optical fiber bundle; or a variety of other polymers.

A "magnetically responsive" material is responsive to a magnetic field. Examples of magnetically responsive solid supports include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP. One commercially available example includes DYNABEADS™ M-280 Streptavidin (superparamagnetic beads coated with streptavidin) from ThermoFisher Scientific. In some examples, the magnetically responsive material is embedded in the shell of a polymer bead. In other examples, the magnetically responsive material is in bead form and is coated with a passivating material, such as silicon oxide or silicon nitrite.

Any example of the solid support 12 may have the form of solid beads, porous beads, or hollow beads.

While not shown in FIG. 1A or in FIG. 1B, the solid support 12 is functionalized with one member of the biotin-streptavidin binding pair or of the desthiobiotin-streptavidin binding pair. A "binding pair" generally refers to two agents (e.g., materials, molecules, moieties) that are capable of attaching to one another. In some examples disclosed herein, the binding pair includes streptavidin and biotin. In other examples disclosed herein, the binding pair includes streptavidin and desthiobiotin. The streptavidin of the binding pair may be positioned at the surface of the solid support 12, and the biotin or desthiobiotin (each of which is represented by reference numeral 20) of the binding pair may be attached to DNA library fragments 14, 14', 14".

In some examples, the streptavidin on the solid support 12 may be multi-functional in that it can i) bind to the biotin or desthiobiotin 20 attached to DNA library fragments 14, 14', 14" and ii) bind to a biotin or desthiobiotin capture site on the sequencing surface of the flow cell. In other examples, the solid support 12 may be functionalized with two different binding pair members, e.g., i) streptavidin (which can bind to the biotin or desthiobiotin 20 attached to DNA library fragments 14, 14', 14"), and ii) another member, which can bind to the capture site on the sequencing surface of the flow cell.

Functionalization of the solid support 12 may involve coating the solid support 12 with streptavidin, alone or in combination with another binding pair member.

The DNA library fragments 14, 14', 14" are attached to the solid support 12. Each DNA library fragment 14, 14', 14" includes a portion (e.g., fragment 16, 16', 16") of a longer piece of genetic material that has adapters (e.g., 18, 18', 18", 22, 22', 22") at the 3' and 5' ends. The DNA library fragments 14, 14', 14" may be prepared using any library preparation technique that fragments a longer piece of genetic material and incorporates the desired adapters to the ends of the fragments. Some suitable library preparation techniques are described in reference to FIG. 1A and FIG. 1B. It is to be understood, however, that other library preparation techniques may also be used.

FIG. 1A depicts an example of a complex 10A including the DNA library fragments 14, 14'. These DNA library fragments 14, 14' are sequencing ready because they include fragments 16, 16' (from the larger nucleic acid sample) and adapters 18, 22 or 18', 22' at the opposed ends of the fragments 16, 16'. The contiguity of the fragments 16, 16' is preserved on the solid support 12.

An example method for making the complex 10A is described herein, but it is to be understood that other methods may be used as long as sequencing-ready nucleic acid fragments 14, 14' are attached to the solid support 12 through the biotin-streptavidin binding pair or desthiobiotin-streptavidin binding pair.

In one example method to form the complex 10A shown in FIG. 1A, an adapter sequence 18, 18' is bound to the biotin or desthiobiotin 20. In an example, this adapter sequence 18, 18' may include a first sequencing primer sequence (e.g., a read 1 sequencing primer sequence) and a first sequence (P5') that is complementary to at least a portion of one of the amplification primers (e.g., P5) on the flow cell (shown in FIG. 3A, FIG. 3B and FIG. 3C). The adapter sequence 18, 18' may also include an index or barcode sequence. The adapter sequence 18, 18' is bound to the biotin or desthiobiotin 20 so that it can, in turn, be bound to the surface of the solid support 12, which includes the streptavidin of the biotin-streptavidin binding pair or the desthiobiotin-streptavidin binding pair.

In this example, a transposome complex (not shown) may also be bound to the solid support 12 at the outset of the library preparation method. Prior to loading the transposome complex on the solid support 12, a partial Y-adapter may be mixed with a transposase enzyme (e.g., two Tn5 molecules) to form a transposome complex. The partial Y-adapter may include two mosaic end sequences (or other transposon end sequences) that are hybridized to each other. One of the mosaic end sequences is referred to as a free mosaic end sequence because it has two free ends, e.g., one that is able to attach to the adapter 18, 18' and another that is able to attach to fragmented DNA strands 16, 16' during tagmentation. This mosaic end sequence is part of a transferred strand. The other of the mosaic end sequences may be attached to another adapter (e.g., 22, 22'), which includes a second sequencing primer sequence (e.g., a read 2 sequencing primer sequence) and a second sequence (P7) that is identical to the at least a portion of another of the amplification primers (P7) on the flow cell. During amplification, the identical sequence enables the formation of a copy that is complementary to at least a portion of the other of the amplification primers (P7) on the flow cell. The adapter sequences 22, 22' are not attached to the fragmented DNA strands 16, 16' during tagmentation, and thus are part of a non-transferred strand.

Loading the transposome complex on the solid support 12 may involve mixing the transposome complex with the solid support 12, and exposing the mixture to suitable conditions for ligating one of free ends of the free mosaic end to the 3'-end of the adapter sequence 18, 18'. Individual transposome complexes may be attached to each of the adapter sequences 18, 18' on the solid support 12.

In this example method to form the complex 10A, a tagmentation process may then be performed. A fluid (e.g., a tagmentation buffer) including the longer nucleic acid sample (e.g., DNA) may be added to the solid support 12 having the adapter sequences 18, 18' and the transposome complexes bound thereto. As the sample contacts the transposome complexes, the longer nucleic acid sample is tagmented. The longer nucleic acid sample is fragmented into fragments 16, 16', and each is tagged, at its 5' end, to the partial Y-adapter (e.g., through ligation of the other free end of the free mosaic (or other transposon) end sequence). Successive tagmentation of the longer nucleic acid sample results in a plurality of bridged molecules between the transposome complexes. The bridged molecules wrap around the solid support 12. The transposome complexes maintain the contiguity of the longer nucleic acid sample as the bridged molecules.

The transposase enzyme may then be removed via sodium dodecyl sulfate (SDS) treatment or heat or proteinase K digestion. Removal of the transposase enzymes leaves the fragments 16, 16' attached to the solid support 12.

To complete the sequencing-ready DNA library fragments 14, 14', further extension and ligation is undertaken to ensure sample fragments 16, 16' are attached to adapter sequences 22 and 22'. The resulting complex 10A is shown in FIG. 1A.

Each sequencing-ready DNA library fragment 14, 14' includes a contiguity preserved library fragment 16, 16' having respective adapter sequences 18 and 22 or 18' and 22' attached at either end. The adapter sequences 18, 18' are those initially bound to the solid support 12, and include the first sequencing primer sequence and the first sequence complementary to one of the flow cell primers. The adapter sequences 18, 18' are attached to the biotin or desthiobiotin of the biotin-streptavidin binding pair or the desthiobiotin-streptavidin binding pair. The adapter sequences 22, 22' are from the partial Y-adapter, and include the second sequence identical to another flow cell primer and the second sequencing primer sequence. Because each sequencing-ready DNA library fragment 14, 14' includes suitable adapters for amplification (e.g., bridge amplification) and sequencing, PCR amplification is not performed. These fragments 14, 14' are thus sequencing-ready. Moreover, because the contiguity preserved library fragments 16, 16' are from the same longer nucleic acid sample, the contiguity of the original sample is preserved and the library fragments 14, 14' may be suitable for linked long read applications.

FIG. 1B illustrates another complex 10B that includes a solid support 12 and sequencing-ready DNA library fragments 14" attached to the solid support 12 using the biotin-streptavidin or desthiobiotin-streptavidin binding pair. In one example, a PCR-free nucleotide library is created in a tube, and then the library is hybridized to the solid support 12 in the tube. In the example shown in FIG. 1B, adapters 18", 22" are added to the library fragments 16" in the tube, primers having the biotin or desthiobiotin 20 attached thereto are hybridized to the adapters 18" in the tube, and then the sequencing-ready nucleic acid fragments 14" are bound to the solid support 12 through the biotin-streptavidin or desthiobiotin-streptavidin binding pair. In another example, the solid support 12 may have primers attached thereto via biotin-streptavidin binding pair (e.g., streptavidin on the support 12 and biotin or desthiobiotin 20 attached to the primer). These primers hybridize to adapters 18" attached to the library fragments 16, 16' (and thus the primer and biotin or desthiobiotin 20 are at one end of the fragments 16, 16' and not at the other). In still other example, extension may be performed using a strand displacing enzyme. This will result in an entirely double stranded library (e.g., no fork or Y-adapter, as shown in FIG. 11B).

As mentioned, other library preparation techniques may also be used, as long as the DNA library fragments 14, 14', 14" are attached to the solid support 12 via the biotin-streptavidin or the desthiobiotin-streptavidin binding pair.

Library Preparation Beads with the Dual Release Mechanism

In some examples disclosed herein, the DNA library fragments 16, 16', 16" are attached to the solid support 12, and are releasable from the solid support 12 with a dual release mechanism. The dual release mechanism includes a cleavage site and a splint, each of which will be described in more detail in reference to FIG. 2A through FIG. 2C.

Figure 2A:
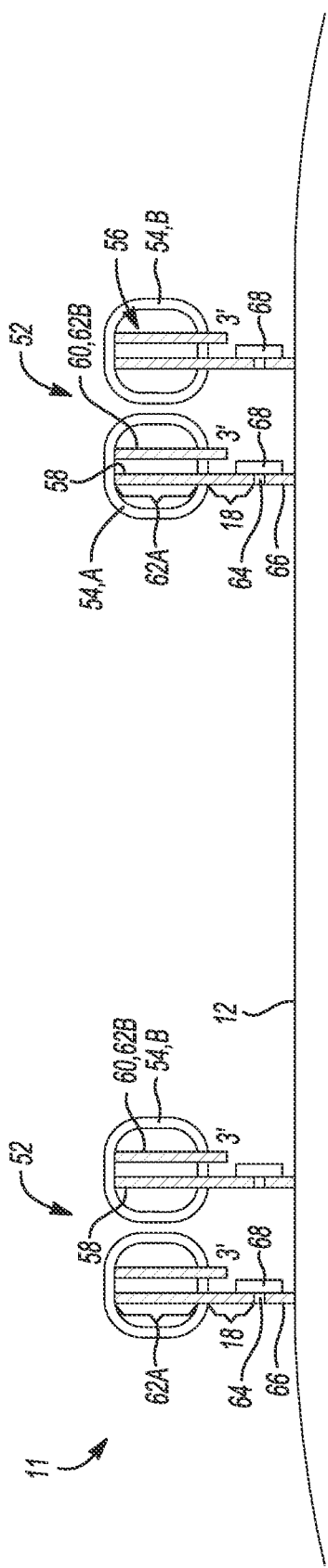
FIG. 2A through FIG. 2C are schematic illustrations of a portion of a library preparation bead prior to tagmentation (2A), during tagmentation (2B), and after tagmentation and during ligation of a non-transferred strand (2C)

An example of the library preparation bead 11 prior to tagmentation is shown in FIG. 2A. The library preparation bead 11 includes a solid support 12 and a transposome complex 52 attached to the solid support 12, the transposome complex 52 includes i) a transposase enzyme 54; ii) a double stranded molecule 56 bound to the transposase enzyme 54, wherein the double stranded molecule 56 includes iia) a transferred strand 58 including a 3' transposon end sequence 62A, an adapter sequence 18, a cleavage site 64, and a 5' linking end sequence 66, wherein the adapter sequence 18 and the 5' linking end sequence 66 flank the cleavage site 64, and iib) a non-transferred strand 60 including a 3' transposon end sequence 62B; and iii) a splint sequence 68 hybridized to at least a portion of the adapter sequence 18 and at least a portion of the 5' linking end sequence 66 such that it splints the cleavage site 64.

The solid support 12 may be any of the examples set forth herein.

As mentioned, the transposome complex 52 includes the transposase enzyme 54. The transposase enzyme 54 may be any of the examples set forth herein. In the example shown in FIG. 2A, the transposome 54 includes a dimer (e.g., of Tn5) with each monomer A, B binding a double stranded molecule 56. As such, this example of the transposome complex 52 includes the transposase enzyme 54 and two double stranded molecules 56 respectively bound to the monomers A, B of the transposase enzyme 54. Each double stranded molecule 56 includes hybridized 3' transposon end sequences 62A, 62B. The 3' transposon end sequence 62A and the 3' transposon end sequence 62B are complementary to each other, and include only nucleotide sequences that are necessary to form the complex with the transposase enzyme 54. As such, the monomers A, B respectively bind to a double stranded molecule 56 through its hybridized 3' transposon end sequences 62A, 62B.

The 3' transposon end sequence 62A of the double stranded molecule 56 makes up a portion of the transferred strand 58. In addition to the 3' transposon end sequence 62A, the transferred strand 58 also includes the adapter sequence 18 linked to the 3' transposon end sequence 62A, the cleavage site 64 linked to the adapter sequence 18, and the 5' linking end sequence 66 linked to the cleavage site 64. As such, the adapter sequence 18 and the 5' linking end sequence 66 flank the cleavage site 64.

The adapter sequence 18 may be any of the examples disclosed herein. When amplification is to be performed on the surface of a flow cell, the adapter sequence 18 may include the first sequencing primer sequence (e.g., a read 1 sequencing primer sequence), a first sequence (e.g., P5') that is complementary to at least a portion of one of the amplification primers (e.g., P5) on the flow cell, and/or an index or barcode sequence.

The cleavage site 64 is selected from the group consisting of a chemically cleavable cleavage site, an enzymatically cleavable cleavage site, and a photocleavable cleavage site. In some examples, the cleavage site 64 is selected from the group consisting of a chemically cleavable cleavage site and an enzymatically cleavable cleavage site. The chemically cleavable cleavage site may include chemically cleavable nucleobases, chemically cleavable modified nucleobases, or chemically cleavable linkers (e.g., between nucleobases). Examples of the chemically cleavable nucleobases, modified nucleobases, or linkers include a vicinal diol (e.g., a 1,2-diol cleavable by periodate), a disulfide, a silane, an azobenzene, a photocleavable group, allyl T (a thymine nucleotide analog having an allyl functionality), allyl ethers, or an azido functional ether. The enzymatically cleavable cleavage site may be an enzymatically cleavable nucleobase. The enzymatically cleavable nucleobase may be susceptible to cleavage by reaction with a glycosylase and an endonuclease, or with an exonuclease. One specific example of the enzymatically cleavable nucleobase is deoxyuracil (dU), which can be targeted by the USER enzyme (a mixture of DNA glycosylase (UDG) and the DNA glycosylase-lyase Endonuclease VIII). Other abasic sites may also be used. Another specific example of the enzymatically cleavable nucleobase is RNA, which can be targeted by RNase.

In other examples, the cleavage site 64 may be a photocleavable site. The photocleavable site may be susceptible to cleavage by exposure to light of a particular wavelength. An example of a photocleavage site is a nitrobenzyl linker with the structure:

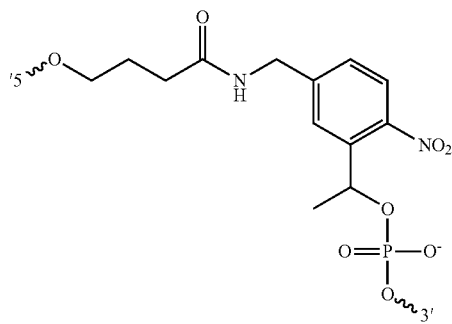

which is cleaved upon irradiation with 365 nm light.

The 5' linking end sequence 66 may be a nucleotide sequence or a binding pair member that can attach to the surface of the solid support 12. In some examples, the solid support 12 may have reactive groups at the surface for covalent coupling to the 5' linking end sequence 66. Examples of such reactive groups include a carboxylic acid, a primary aliphatic amine, an aromatic amine, an aromatic chloromethyl (e.g., vinyl benzyl chloride), an amide, a hydrazide, an aldehyde, a hydroxyl, a thiol, and an epoxy. These reactive group(s) may be inherently present at the surface of the solid support 12, or may be incorporated on the surface of the solid support 12 through any suitable functionalization technique (e.g., chemical reaction, coating the solid support 12 with a reactive group-containing polymer, etc.). In other examples, the solid support 12 may be coated with one member of a binding pair, and the 5' linking end sequence 66 may be attached to the other member of the binding pair.

The splint sequence 68 is a nucleotide sequence having a portion that is complementary to at least a portion of the adapter sequence 18 and a portion that is complementary to at least a portion of the 5' linking end sequence 66. The respective portions of the splint sequence 68 are hybridized to the respective portions of the adapter sequence 18 and of the 5' linking end sequence 66 such that the splint sequence 68 bridges the cleavage site 64. The portion of the splint sequence 68 that splints or bridges the cleavage site 64 is not attached to the cleavage site 64. While not shown in FIG. 2A through FIG. 2C, some examples of the splint 68 may include a portion that is complementary to the entire 5' linking end sequence 66. In this example, the 3' end of the splint 68 may be attached to the solid support 12 through a binding pair or a covalent bond.

The 3' transposon end sequence 62B of the double stranded molecule 56 makes up the entire non-transferred strand 60.

Figure 2B:
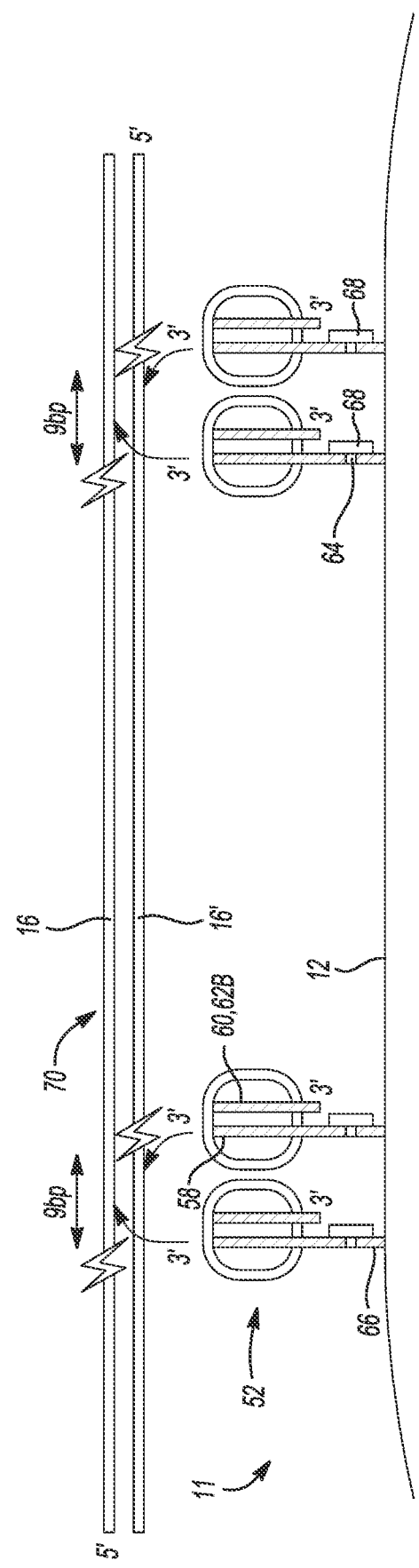

FIG. 2B schematically illustrates the tagmentation process involving library preparation beads 11. A DNA sample 70 may be mixed with the library preparation beads 11. The DNA sample 70 may be DNA or may be complementary DNA (cDNA) derived from an RNA sample. Converting the RNA sample to the cDNA sample may be done using reverse transcription, which utilizes a reverse transcriptase enzyme. In some examples, a kit for reverse transcription and second strand synthesis is used. In these examples, the high capacity cDNA reverse transcription kit, from ThermoFisher Scientific, may be used. In other examples, a kit for reverse transcription and template switch (for the second strand) is used. In these examples, the template switching RT enzyme mix, from New England Biolabs, may be used.

Figure 2C:
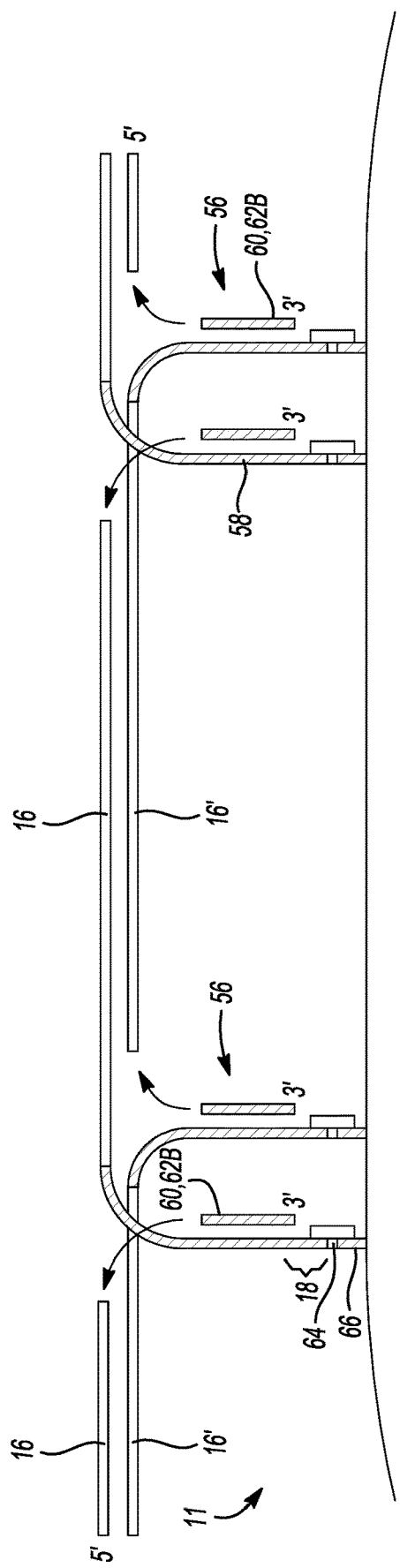

The DNA sample 70 may be incorporated into a carrier liquid (e.g., a tagmentation buffer) to generate a library preparation fluid. This library preparation fluid may be mixed with the library preparation beads 11. The transposome complex 52 binds the sample DNA 70 and generates two nicks in the DNA backbone, which are presented by the lightning bolts in FIG. 2B. This creates the fragments 16, 16'. In the example shown in FIG. 2B, the nicks are 9 bases apart on either strand. It is to be understood that the transposome complex 52 can generate a gap of 7, 8, 9, 10, 11, or 12 bp between nicks. One of the two strands (e.g., transferred strand 58) of each transposome complex 52 is ligated to the 5' end of each fragment 16, 16' at each nick position. The attachment of the transferred strands 58 to each fragment 16, 16' is depicted in FIG. 2C.

The transposase enzyme 54 (both monomers A and B) may then be removed via sodium dodecyl sulfate (SDS) treatment or heat or proteinase K digestion. Removal of the transposase enzymes 54 leaves the fragments 16, 16' attached to the solid support 12 through the transferred strands 58.

To complete the formation of sequencing ready fragments 14, 14' (which include adapters 18, 22 at both ends similar to the example shown in FIG. 1A), further extension and ligation is undertaken to ensure that the sample fragments 16, 16' are attached to the non-transferred strand 60 and/or an additional adapter sequence(s) 22. In some instances, the non-transferred strand 60 is removed (e.g., via heat or enzymatic digestion) and then the adapter sequence(s) 22 is/are added (e.g., via extension ligation) to the 3' end of the fragments 16, 16'. In other instances, the non-transferred strand 60 is ligated to the 3' end of the fragments 16, 16' and then the adapter(s) 22 is/are added to the now ligated non-transferred strand 60.

Figure 4:
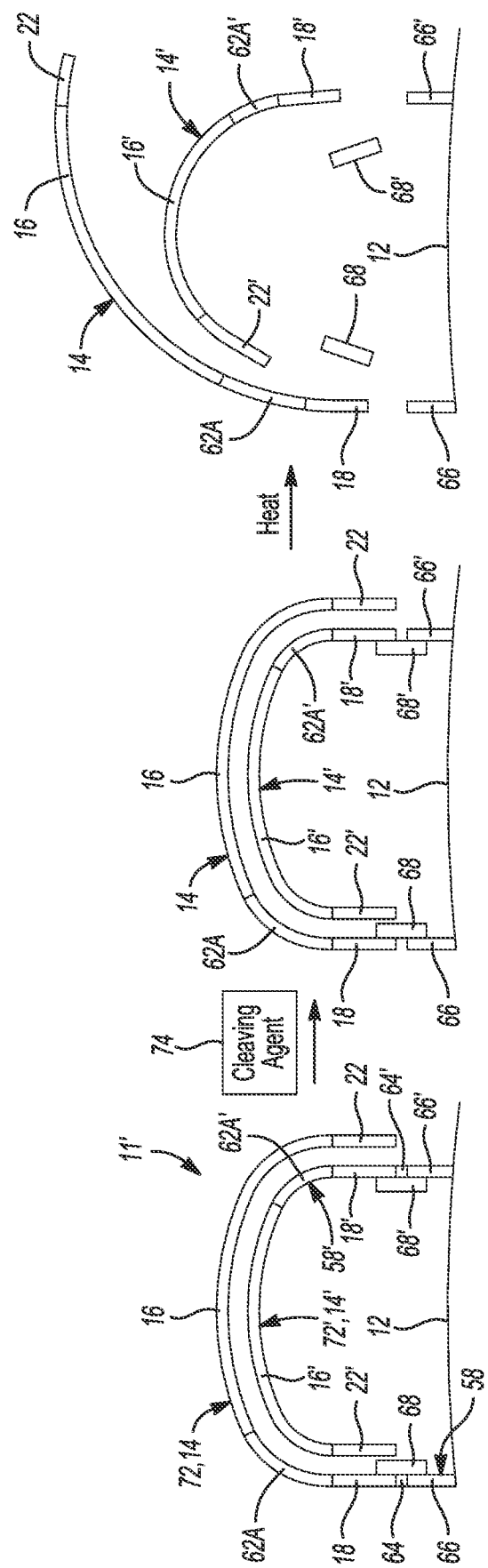
FIG. 4 is a schematic flow diagram illustrating the dual mechanism release of sequencing-ready library fragments from prepped library preparation beads.

When it is desirable to release the sequencing ready fragments 14, 14' from the solid support 12, the dual release mechanism may be used as described further herein in reference to FIG. 4.

Flow Cell

In some examples, the complexes 10A, 10B or prepped library preparation beads 11' (shown in FIG. 4) are introduced into a flow cell for amplification and sequencing. A top view of an example of the flow cell 24 is shown in FIG.

3A. As will be discussed in reference to FIG. 3B and FIG. 3C, some examples of the flow cell 24 include two sequencing opposed sequencing surfaces. An example of non-patterned sequencing surfaces 30, 30' are shown in FIG. 3B, and an example of patterned sequencing surfaces 32, 32' are shown in FIG. 3C. Each sequencing surface 30, 30' or 32, 32' is supported by a substrate (generally shown as 26 in FIG. 3A), and a flow channel (generally shown as 28 in FIG. 3A) is defined between the sequencing surfaces 30, 30' or 32, 32'. In other examples, the flow cell 24 includes one sequencing surface supported by a substrate and a lid attached to the substrate. In these examples, the flow channel 28 is defined between the sequencing surface 30 or 32 and the lid.

In any of the examples, the substrate 26 may be a single layer/material. Examples of the single layer substrate are shown at reference numeral 26A and 26A' in FIG. 3B. Examples of suitable single layer substrates 26A, 26A' include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) (TaOX), hafnium oxide ($HfO_2$), carbon, metals, inorganic glasses, or the like.

The substrate 26 may also be a multi-layered structure. Examples of the multi-layered substrate are shown at reference numeral 26B and 26B' in FIG. 3C. Some examples of the multi-layered structure 26B, 26B' include glass or silicon, with a coating layer of tantalum oxide or another ceramic oxide at the surface. With specific reference to FIG. 3C, other examples of the multi-layered structure 26B, 26B' include an underlying support 34, 34' having a patterned resin 36, 36' thereon. Still other examples of the multi-layered substrate 26B, 26B' may include a silicon-on-insulator (SOI) substrate.

In an example, the substrate 26 (whether single or multi-layered) may have a diameter ranging from about 2 mm to about 300 mm, or a rectangular sheet or panel having its largest dimension up to about 10 feet (~3 meters). In an example, the substrate 26 is a wafer having a diameter ranging from about 200 mm to about 300 mm. In another example, the substrate 24 is a die having a width ranging from about 0.1 mm to about 10 mm. While example dimensions have been provided, it is to be understood that a substrate 26 with any suitable dimensions may be used. For another example, a panel may be used that is a rectangular support, which has a greater surface area than a 300 mm round wafer.

Figure 3A:
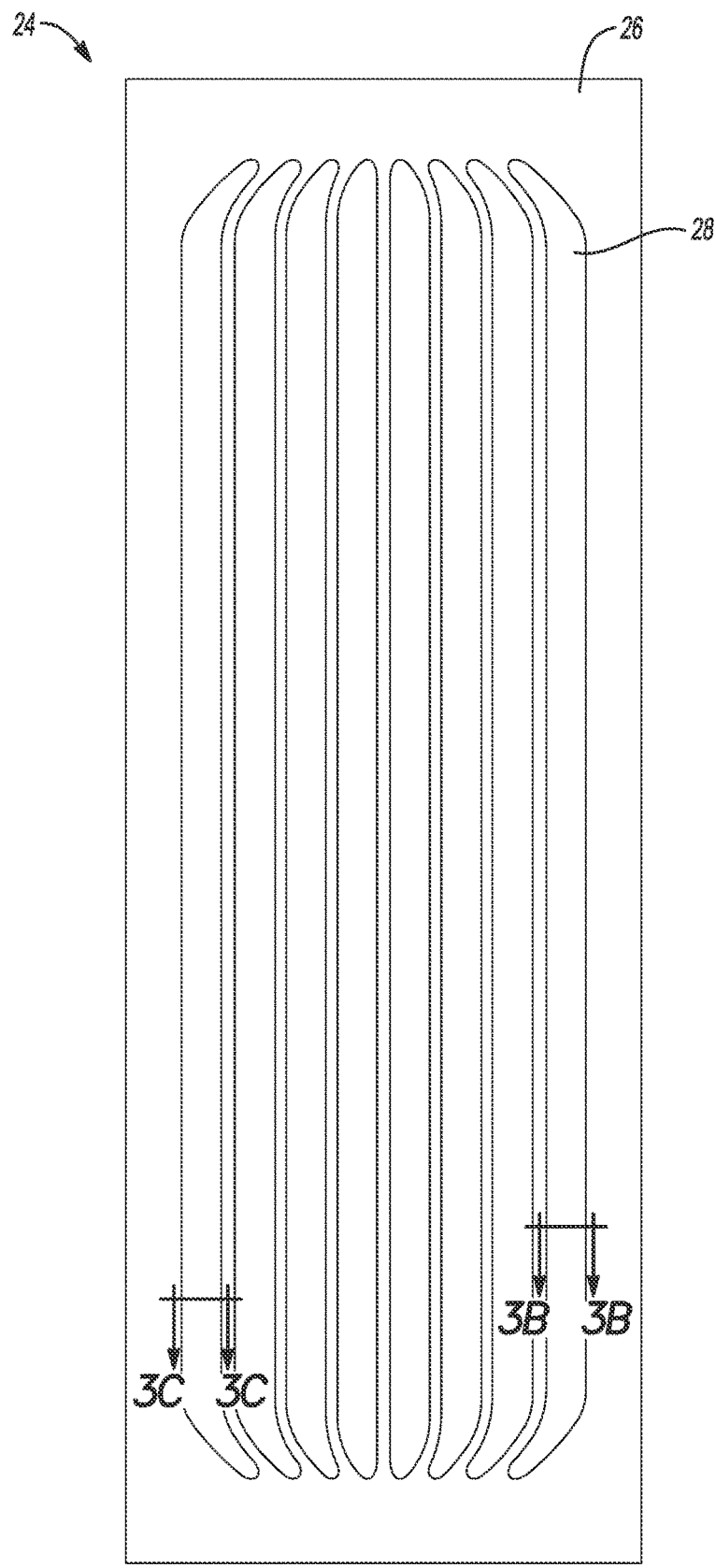
FIG. 3A is a top view of an example of a flow cell.
Figure 3B:
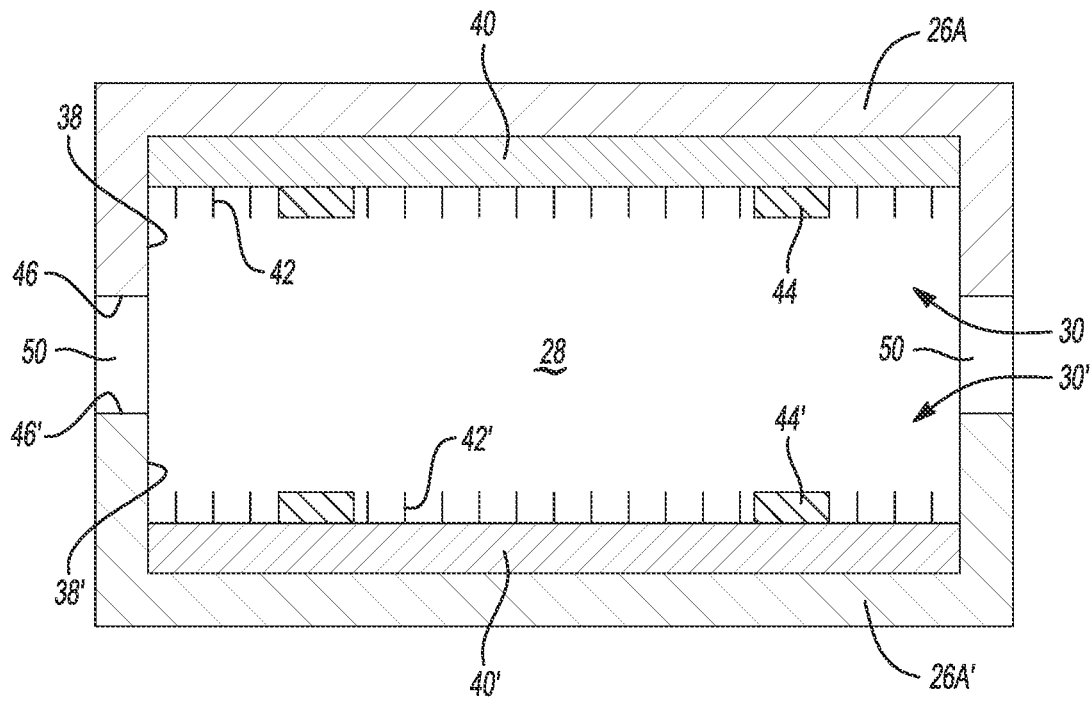
FIG. 3B is an enlarged, cross-sectional view, taken along the 3B-3B line of FIG. 3A, of an example of a flow channel and non-patterned sequencing surfaces.
Figure 3C:
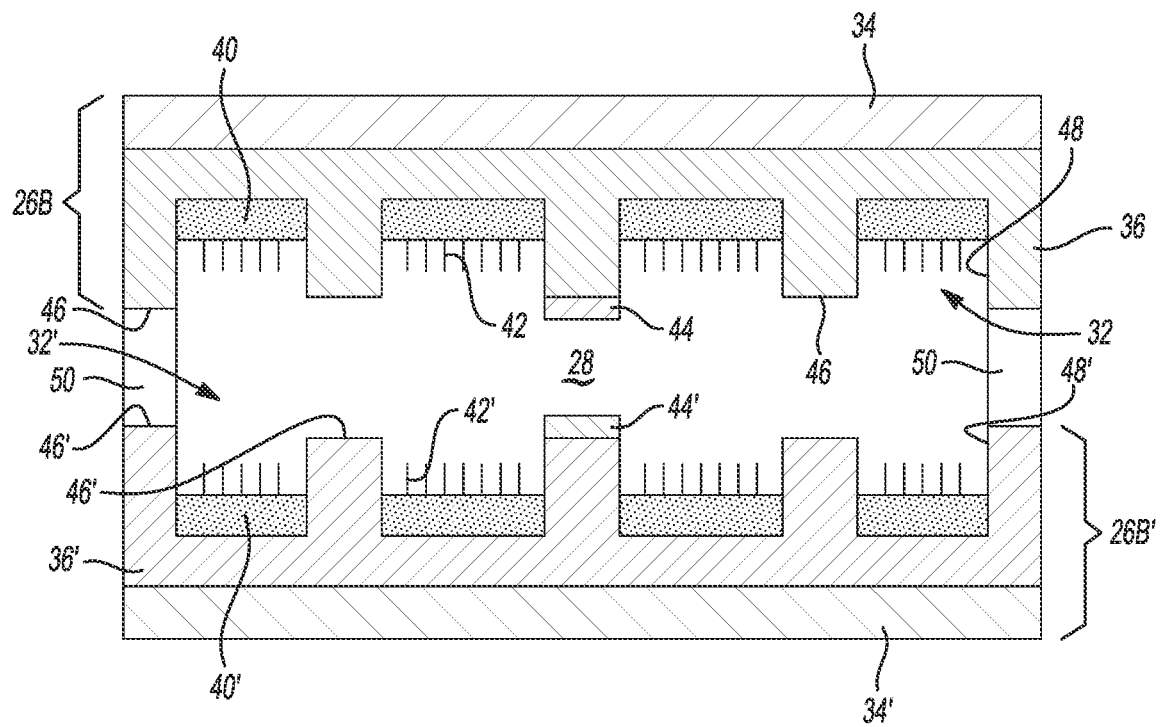
FIG. 3C is an enlarged, cross-sectional view, taken along the 3C-3C line of FIG. 3A, of an example of a flow channel and patterned sequencing surfaces.

In the example shown in FIG. 3A, the flow cell 24 includes flow channels 28. While several flow channels 28 are shown, it is to be understood that any number of channels 28 may be included in the flow cell 24 (e.g., a single channel 28, four channels 28, etc.). In some of the examples disclosed herein, each flow channel 28 is an area defined between two sequencing surfaces (e.g., 30 and 30' or 32 and 32') and by two attached substrates (e.g., 26A and 26A' or 26B and 26B'). In other of the examples disclosed herein, each flow channel 28 is an area defined between one sequencing surface (e.g., 30 or 32) and a lid. The fluids described herein can be introduced into and removed from the flow channel(s) 28. Each flow channel 28 may be isolated from each other flow channel 28 in a flow cell 24 so that fluid introduced into any particular flow channel 28 does not flow into any adjacent flow channel 28.

A portion of the flow channel 28 may be defined in the substrate 26 using any suitable technique that depends, in part, upon the material(s) of the substrate 26. In one example, a portion of the flow channel 28 is etched into a glass substrate 26. In another example, a portion of the flow channel 28 may be patterned into a resin 36, 36' of a multi-layered substrate 28B, 28B' using photolithography, nanoimprint lithography, etc. In still another example, a separate material (e.g., material 50 in FIG. 3B and FIG. 3C) may be applied to the substrate 26 so that the separate material defines at least a portion of the walls of the flow channel 28.

In an example, the flow channel 28 has a rectilinear configuration. The length and width of the flow channel 28 may be smaller, respectively, than the length and width of the substrate 26 so that portion of the substrate surface surrounding the flow channel 28 is available for attachment to another substrate 26. In some instances, the width of each flow channel 28 can be at least about 1 mm, at least about 2.5 mm, at least about 5 mm, at least about 7 mm, at least about 10 mm, or more. In some instances, the length of each flow channel 28 can be at least about 10 mm, at least about 25 mm, at least about 50 mm, at least about 100 mm, or more. The width and/or length of each flow channel 28 can be greater than, less than or between the values specified above. In another example, the flow channel 28 is square (e.g., 10 mm×10 mm).

The depth of each flow channel 28 can be as small as a few monolayers thick, for example, when microcontact, aerosol, or inkjet printing is used to deposit a separate material that defines the flow channel walls. For other examples, the depth of each flow channel 28 can be about 1 μm, about 10 μm, about 50 μm, about 100 μm, or more. In an example, the depth may range from about 10 μm to about 100 μm. In another example, the depth is about 5 μm or less. It is to be understood that the depth of each flow channel 28 be greater than, less than or between the values specified above. The depth of the flow channel 28 may also vary along the length and width of the flow cell 24, e.g., when a patterned sequencing surface 32, 32' is used.

FIG. 3B illustrates a cross-sectional view of the flow cell 24 including non-patterned opposed sequencing surfaces 30, 30'. In an example, each of these surfaces 30, 30' may be prepared on the substrate 26A, 26A', and then the substrates 26A, 26A' may be attached to one another to form an example of the flow cell 24. Any suitable bonding material 50, such as an adhesive, a radiation-absorbing material that aids in bonding, etc., may be used to bond the substrates 26A, 26B together.

In the example shown in FIG. 3B, a portion of the flow channel 28 is defined in each of the single layer substrates 26A, 26A'. For example, each substrate 26A, 26A' may have a concave region 38, 38' defined therein where the components of the sequencing surface 30, 30' may be introduced. It is to be understood that any space within the concave region 38, 38' not occupied by the components of the sequencing surface 30, 30' may be considered to be part of the flow channel 28.

The sequencing surfaces 30, 30' include a polymeric hydrogel 40, 40', amplification primers 42, 42' attached to the polymeric hydrogel 40, 40', and chemical capture sites 44, 44'.

An example of the polymeric hydrogel 40, 40' includes an acrylamide copolymer, such as poly(N-(5-azidoacetamidylpentyl)acrylamide-co-acrylamide, PAZAM. PAZAM and some other forms of the acrylamide copolymer are represented by the following structure (I):

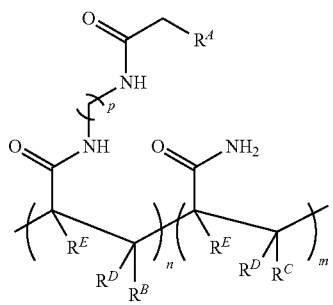

wherein:
R$^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;

R$^B$ is H or optionally substituted alkyl;

R$^C$, R$^D$, and R$^E$ are each independently selected from the group consisting of H and optionally substituted alkyl;

each of the —(CH$_2$)$_p$— can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in structure (1) are representative, and the monomeric subunits may be present in any order in the polymer structure (e.g., random, block, patterned, or a combination thereof).

The molecular weight of PAZAM and other forms of the acrylamide copolymer may range from about 5 kDa to about 1500 kDa or from about 10 kDa to about 1000 kDa, or may be, in a specific example, about 312 kDa.

In some examples, PAZAM and other forms of the acrylamide copolymer are linear polymers. In some other examples, PAZAM and other forms of the acrylamide copolymer are lightly cross-linked polymers.

In other examples, the polymeric hydrogel 40, 40' may be a variation of the structure (1). In one example, the acrylamide unit may be replaced with N,N-dimethylacrylamide

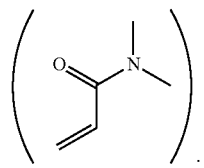

In this example, the acrylamide unit in structure (1) may be replaced with

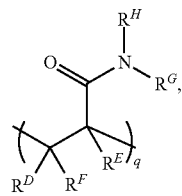

where R$^D$, R$^E$, and R$^F$ are each H or a C1-C6 alkyl, and R$^G$ and R$^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (1) may include

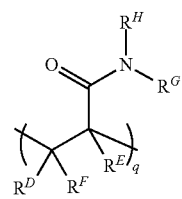

in addition to the recurring "n" and "m" features, where R$^D$, R$^E$, and R$^F$ are each H or a C1-C6 alkyl, and R$^G$ and R$^H$ are each a C1-C6 alkyl. In this example, q may be an integer in the range of 1 to 100,000.

As another example of the polymeric hydrogel 40, 40', the recurring "n" feature in structure (1) may be replaced with a monomer including a heterocyclic azido group having structure (II):

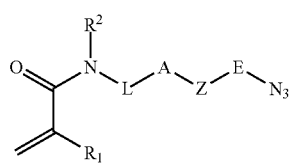

wherein R$^1$ is H or a C1-C6 alkyl; R$_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 ring members present as a single cyclic structure or a fused structure. Some specific examples of Z include pyrrolidinyl, pyridinyl, or pyrimidinyl.

As still another example, the polymeric hydrogel 40, 40' may include a recurring unit of each of structure (III) and (IV):

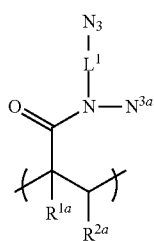

and

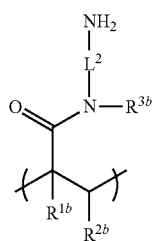

wherein each of $R^{1a}$, $R^{2a}$, $R^{1b}$ and $R^{2b}$ is independently selected from hydrogen, an optionally substituted alkyl or optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

It is to be understood that other molecules may be used to form the polymeric hydrogel 40, 40', as long as they are functionalized to graft oligonucleotide primers 42, 42' thereto. Other examples of suitable polymer layers include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymeric hydrogels 42 include mixed copolymers of acrylamides and acrylates. A variety of polymer architectures containing acrylic monomers (e.g., acrylamides, acrylates etc.) may be utilized in the examples disclosed herein, such as branched polymers, including star polymers, star-shaped or star-block polymers, dendrimers, and the like. For example, the monomers (e.g., acrylamide, etc.) may be incorporated, either randomly or in block, into the branches (arms) of a star-shaped polymer.

To introduce the polymeric hydrogel 40, 40' into the concave regions 38, 38', a mixture of the polymeric hydrogel 40, 40' may be generated and then applied to the respective substrates 26A, 26A' (having the concave regions 38, 38' defined therein). In one example, the polymeric hydrogel 40, 40' may be present in a mixture (e.g., with water or with ethanol and water). The mixture may then be applied to the respective substrate surfaces (including in the concave regions 38, 38') using spin coating, or dipping or dip coating, or flow of the material under positive or negative pressure, or another suitable technique. These types of techniques blanketly deposit the polymeric hydrogel 40, 40' on the substrate respective substrates 26A, 26A' (e.g., in the concave regions 38, 38' and on interstitial regions 46, 46' adjacent thereto). Other selective deposition techniques (e.g. involving a mask, controlled printing techniques, etc.) may be used to specifically deposit the polymeric hydrogel in the concave regions 38, 38' and not on the interstitial regions 46, 46'.

In some examples, the substrate surface (including the concave regions 38, 38') may be activated, and then the mixture (including the polymeric hydrogel 40, 40' may be applied thereto. In one example, a silane or silane derivative (e.g., norbornene silane) may be deposited on the substrate surface using vapor deposition, spin coating, or other deposition methods. In another example, the substrate surface may be exposed to plasma ashing to generate surface-activating agent(s) (e.g., —OH groups) that can adhere to the polymeric hydrogel 40, 40'.

Depending upon the chemistry of the polymeric hydrogel 40, 40', the applied mixture may be exposed to a curing process. In an example, curing may take place at a temperature ranging from room temperature (e.g., from about 18° C. to about 25° C.) to about 95° C. for a time ranging from about 1 millisecond to about several days.

Polishing may then be performed in order to remove the polymeric hydrogel 40, 40' from the interstitial regions 46, 46' at the perimeter of the concave regions 38, 38', while leaving the polymeric hydrogel 40, 40' on the surface in the concave regions 38, 38' at least substantially intact.

The sequencing surfaces 30, 30' also include amplification primers 42, 42' attached to the polymeric hydrogel 40, 40'. A grafting process may be performed to graft the amplification primers 42, 42' to the polymeric hydrogel 40, 40' in the concave regions 38, 38'. In an example, the amplification primers 42, 42' can be immobilized to the polymeric hydrogel 40, 40' by single point covalent attachment at or near the 5' end of the primers 42, 42'. This attachment leaves i) an adapter-specific portion of the primers 42, 42' free to anneal to its cognate sequencing-ready nucleic acid fragment and ii) the 3' hydroxyl group free for primer extension. Any suitable covalent attachment may be used for this purpose. Examples of terminated primers that may be used include alkyne terminated primers (e.g., which may attach to an azide surface moiety of the polymeric hydrogel 40, 40'), or azide terminated primers (e.g., which may attach to an alkyne surface moiety of the polymeric hydrogel 40, 40').

Specific examples of suitable primers 42, 42' include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™ and other instrument platforms. Both P5 and P7 primers may be grafted to each of the polymeric hydrogels 40, 40'.

In an example, grafting may involve flow through deposition (e.g., using a temporarily bound lid), dunk coating, spray coating, puddle dispensing, or by another suitable method that will attach the primer(s) 42, 42' to the polymeric hydrogel 40, 40'. Each of these example techniques may utilize a primer solution or mixture, which may include the primer(s) 42, 42', water, a buffer, and a catalyst. With any of the grafting methods, the primers 42, 42' react with reactive groups of the polymeric hydrogel 40, 40' in the concave region 38, 38' and have no affinity for the surrounding substrate 26A, 26A'. As such, the primers 42, 42' selectively graft to the polymeric hydrogel 40, 40'.

In the example shown in FIG. 3B, the chemical capture site 44, 44' includes a chemical capture agent that is attached to or applied on at least a portion of the polymeric hydrogel

40, 40'. Any example of the chemical capture agents disclosed herein may be used. In some examples, the chemical capture agent may be biotin, which can help to attach the streptavidin coated complexes 10A, 10B to the flow cell sequencing surface(s) 30, 30' or 32, 32'. In other examples, the chemical capture agent may be another member of a binding pair other than the biotin-streptavidin binding pair. In these other examples, the complexes 10A, 10B include two different binding pair members, e.g., i) streptavidin (which can bind to the biotin 20 attached to DNA library fragments 14, 14', 14"), and ii) another member, which can bind to the chemical capture agent of the capture site 44, 44' on the sequencing surface of the flow cell. In these other examples, the chemical capture agent may be a non-biotin member of a binding pair, where the other member of the binding pair is attached to the solid support 12 in addition to the streptavidin.

In some examples, free functional groups (e.g., those not attached to primers 42, 42') of the polymeric hydrogel 40, 40' may be functionalized with the chemical capture agent so that several chemical capture sites 44, 44' are formed across the surface of the polymeric hydrogel 40, 40'. In an example, alkyne-PEG-biotin linkers or alkyne-biotin free azide groups may be covalently attached to free azides on the polymeric hydrogel 40, 40' using click chemistry. In another example, primers that are complementary to the amplification primers 42, 42' may have the chemical capture agent (e.g., biotin or another member of a binding pair) attached thereto. These complementary primers may be hybridized to some of the amplification primers 42, 42' to form the chemical capture site 44, 44'.

In another example, the chemical capture agent may be deposited in a desirable location using microcontact printing, aerosol printing, etc. to form the chemical capture site(s) 44, 44'. In still another example, a mask (e.g., a photoresist) may be used to define the space/location where the chemical capture agent will be deposited, and thus where the chemical capture site 44, 44' will be formed. The chemical capture agent may then be deposited, and the mask removed (e.g., via lift-off, dissolution, or another suitable technique). In this example, the chemical capture site 44, 44' may include a monolayer or thin layer of the chemical capture agent.

FIG. 3C illustrates a cross-sectional view of the flow cell 24 including patterned opposed sequencing surfaces 32, 32'. In an example, each of these surfaces 32, 32' may be prepared on the substrate 26B, 26B', and then the substrates 26B, 26B' may be attached to one another (e.g., via material 50) to form an example of the flow cell 24.

In the example shown in FIG. 3C, the flow cell 24 includes the multi-layer substrate 26B, 26B', each of which includes the support 34, 34' and the patterned material 36, 36' positioned on the support 34, 34'. The patterned material 36, 36' defines depressions 48, 48' separated by interstitial regions 46, 46'.

In the example shown in FIG. 3C, the patterned material 36, 36' is respectively positioned on the support 34, 34'. It is to be understood that any material that can be selectively deposited, or deposited and patterned to form the depressions 48, 48' and the interstitial regions 46, 46' may be used for the patterned material 36, 36'.

As one example, an inorganic oxide may be selectively applied to the support 34, 34' via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example, a resin may be applied to the support 34, 34' and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane resin-based resin, a non-polyhedral oligomeric silsesquioxane epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (commercially available under the tradename POSS® from Hybrid Plastics) refers to a chemical composition that is a hybrid intermediate (e.g., $RSiO_{1.5}$) between that of silica ($SiO_2$) and silicone ($R_2SiO$). An example of a polyhedral oligomeric silsesquioxane can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for a polyhedral oligomeric silsesquioxane include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units. The average cage content can be adjusted during the synthesis, and/or controlled by purification methods, and a distribution of cage sizes of the monomeric unit(s) may be used in the examples disclosed herein.

As shown in FIG. 3C, the patterned material 36, 36' includes the depressions 48, 48' respectively defined therein, and interstitial regions 46, 46' separating adjacent depressions 48, 48'. Many different layouts of the depressions 48, 48' may be envisaged, including regular, repeating, and non-regular patterns. In an example, the depressions 48, 48' are disposed in a hexagonal grid for close packing and improved density. Other layouts may include, for example, rectilinear (rectangular) layouts, triangular layouts, and so forth. In some examples, the layout or pattern can be an x-y format of depressions 48, 48' that are in rows and columns. In some other examples, the layout or pattern can be a repeating arrangement of depressions 48, 48' and/or interstitial regions 46, 46'. In still other examples, the layout or pattern can be a random arrangement of depressions 48, 48' and/or interstitial regions 46, 46'. The pattern may include stripes, swirls, lines, triangles, rectangles, circles, arcs, checks, plaids, diagonals, arrows, squares, and/or crosshatches.

The layout or pattern of the depressions 48, 48' may be characterized with respect to the density of the depressions 48, 48' (e.g., number of depressions 48, 48') in a defined area. For example, the depressions 48, 48' may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$ about 5 million per $mm^2$, about 10 million per $mm^2$, about 50 million per $mm^2$, or more, or less. It is to be further understood that the density of depressions 48,

48' in the patterned material 36, 36' can be between one of the lower values and one of the upper values selected from the ranges above. As examples, a high density array may be characterized as having depressions 48, 48' separated by less than about 100 nm, a medium density array may be characterized as having depressions 48, 48' separated by about 400 nm to about 1 µm, and a low density array may be characterized as having depressions 48, 48' separated by greater than about 1 µm. While example densities have been provided, it is to be understood that any suitable densities may be used. The density of the depressions 48, 48' may depend, in part, on the depth of the depressions 48, 48'. In some instances, it may be desirable for the spacing between depressions 48, 48' to be even greater than the examples listed herein.

The layout or pattern of the depressions 48, 48' may also or alternatively be characterized in terms of the average pitch, or the spacing from the center of the depression 48, 48' to the center of an adjacent depression 48, 48' (center-to-center spacing) or from the edge of one depression 48, 48' to the edge of an adjacent depression 48, 48' (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of depressions 48, 48' can be between one of the lower values and one of the upper values selected from the ranges above. In an example, the depressions 48, 48' have a pitch (center-to-center spacing) of about 1.5 µm. While example average pitch values have been provided, it is to be understood that other average pitch values may be used.

The size of each depression 48, 48' may be characterized by its volume, opening area, depth, and/or diameter.

Each depression 48, 48' can have any volume that is capable of confining at least some fluid that is introduced into the flow cell 24. The minimum or maximum volume can be selected, for example, to accommodate the throughput (e.g., multiplexity), resolution, nucleotides, or analyte reactivity expected for downstream uses of the flow cell 24. For example, the volume can be at least about $1\times10^{-3}$ µm$^3$, at least about $1\times10^{-2}$ µm$^3$, at least about 0.1 µm$^3$, at least about 1 µm$^3$, at least about 10 µm$^3$, at least about 100 µm$^3$, or more. Alternatively or additionally, the volume can be at most about $1\times10^4$ µm$^3$, at most about $1\times10^3$ µm$^3$, at most about 100 µm$^3$, at most about 10 µm$^3$, at most about 1 µm$^3$, at most about 0.1 µm$^3$, or less.

The area occupied by each depression opening can be selected based upon similar criteria as those set forth above for the volume. For example, the area for each depression opening can be at least about $1\times10^{-3}$ µm$^2$, at least about $1\times10^{-2}$ µm$^2$, at least about 0.1 µm$^2$, at least about 1 µm$^2$, at least about 10 µm$^2$, at least about 100 µm$^2$, or more. Alternatively or additionally, the area can be at most about $1\times10^3$ µm$^2$, at most about 100 µm$^2$, at most about 10 µm$^2$, at most about 1 µm$^2$, at most about 0.1 µm$^2$, at most about $1\times10^{-2}$ µm$^2$, or less. The area occupied by each depression opening can be greater than, less than or between the values specified above.

The depth of each depression 48, 48' can be large enough to house some of the polymeric hydrogel 40, 40'. In an example, the depth may be at least about 0.1 µm, at least about 0.5 µm, at least about 1 µm, at least about 10 µm, at least about 100 µm, or more. Alternatively or additionally, the depth can be at most about $1\times10^3$ µm, at most about 100 µm, at most about 10 µm, or less. In some examples, the depth is about 0.4 µm. The depth of each depression 48, 48' can be greater than, less than or between the values specified above.

In some instances, the diameter or length and width of each depression 48, 48' can be at least about 50 nm, at least about 0.1 µm, at least about 0.5 µm, at least about 1 µm, at least about 10 µm, at least about 100 µm, or more. Alternatively or additionally, the diameter or length and width can be at most about $1\times10^3$ µm, at most about 100 µm, at most about 10 µm, at most about 1 µm, at most about 0.5 µm, at most about 0.1 µm, or less (e.g., about 50 nm). In some examples, the diameter or length and width is about 0.4 µm. The diameter or length and width of each depression 48, 48' can be greater than, less than or between the values specified above.

In this example, at least some of components of the sequencing surface 32, 32' may be introduced into the depressions 48, 48'. It is to be understood that any space within the depressions 48, 48' not occupied by the components of the sequencing surface 32, 32' may be considered to be part of the flow channel 28.

In the example shown in FIG. 3C, the polymeric hydrogel 40, 40' is positioned within each of the depressions 48, 48'. The polymeric hydrogel 40, 40' may be applied as described in reference to FIG. 3B, so that the polymeric hydrogel 40, 40' is present in the depressions 48, 48' and not present on the surrounding interstitial regions 46, 46'.

In the example shown in FIG. 3C, the primers 42, 42' may be grafted to the polymeric hydrogel 40, 40' within each of the depressions 48, 48'. The primers 42, 42' may be applied as described in reference to FIG. 3B, and thus will graft to the polymeric hydrogel 40, 40' and not to the surrounding interstitial regions 46, 46'.

In the example shown in FIG. 3C, the chemical capture site 44, 44' is a chemical capture agent that is applied on at least some of the interstitial regions 46, 46'. For example, the chemical capture agent may be deposited on at least some of the interstitial regions 46, 46' using microcontact printing, aerosol printing, etc. to form the chemical capture site(s) 44, 44'. In still another example, a mask (e.g., a photoresist) may be used to define the space/location where the chemical capture agent will be deposited, and thus where the chemical capture site 44, 44' will be formed. The chemical capture agent may then be deposited, and the mask removed (e.g., via lift-off, dissolution, or another suitable technique).

In other examples, the chemical capture site 44, 44' is a chemical capture agent that is attached to free functional groups (e.g., those not attached to primers 42, 42') of the polymeric hydrogel 40, 40'. In still other examples, the chemical capture site 44, 44' is a chemical capture agent that is attached to primers that are hybridized to some of the amplification primers 42, 42'. In these examples, the chemical capture site 44, 44' will be present in the depressions 48, 48' and not on the interstitial regions 46, 46'.

Any examples of the chemical capture agent disclosed herein may be used in the example shown in FIG. 3C. The chemical capture agent may be biotin or another member of a binding pair, depending, in part, how the solid support 12 is functionalized.

As shown in FIG. 3B and FIG. 3C, the substrates 26A and 26A' or 26B and 26B' are attached to one another so that the sequencing surfaces 30 and 30' or 32 and 32' face each other with the flow channel 28 defined therebetween.

The substrates 26A and 26A' or 26B and 26B' may be bonded to each other at some or all of the interstitial regions 46, 46'. The bond that is formed between the substrates 26A and 26A' or 26B and 26B' may be a chemical bond, or a mechanical bond (e.g., using a fastener, etc.).

Any suitable technique, such as laser bonding, diffusion bonding, anodic bonding, eutectic bonding, plasma activation bonding, glass frit bonding, or other methods known in the art may be used to bond the substrates 26A and 26A' or 26B and 26B' together. In an example, a spacer layer (e.g., material 50) may be used to bond the substrates 26A and 26A' or 26B and 26B'. The spacer layer may be any material 50 that will seal at least some portion of the substrates 26A and 26A' or 26B and 26B' together. In some examples, the spacer layer can be a radiation-absorbing material that aids in bonding.

While not shown, it is to be understood that a lid may be bonded to one of the substrate 26A' or 26B' so that the flow cell has one sequencing surface.

Method and Kit Involving Target Materials with Biotin-Streptavidin Bonds

An example of the method that utilizes the first example of the cleavage composition generally includes introducing library fragments 14, 14', 14" to a flow cell 24, wherein the library fragments 14, 14', 14" are attached to streptavidin coated solid supports 12; introducing a biotin-streptavidin cleavage composition to the flow cell 24, the biotin-streptavidin cleavage composition including from about 10% by volume to about 50% by volume of a formamide reagent and a balance of a salt buffer; and allowing the biotin-streptavidin cleavage composition to incubate in the flow cell at a temperature ranging from about 60° C. to about 70° C., thereby causing at least some of the library fragments 14, 14', 14" to release from the solid supports 12 and to seed to amplification primers 42, 42' on a surface of the flow cell 24.

Prior to performing the method, the library fragments 14, 14', 14" may be prepared and attached to the solid support 12. In one example, the complexes 10A or 10B may be prepared using a nucleic acid sample and a library preparation fluid including a plurality of solid supports 12 therein.

In some examples, each of the solid supports 12 in the library preparation fluid may have, for example, adapters (such as adapters 18) attached thereto, as described in reference to FIG. 1A. Tagmentation and library preparation may be performed as defined in FIG. 1A to form the complexes 10A. The nucleic acid sample 70, the solid supports 12, the partial Y-adapters, and the transposase enzyme may be contained in separate fluids until it is desirable to form the complexes 10A.

In other examples, each of the solid supports 12 in the library preparation fluid may have, for example, oligonucleotides attached thereto. In some examples, PCR-free nucleotide library preparation may take place separately from the solid supports 12, and then the prepared library fragments can be hybridized to the oligonucleotides (primers) attached via biotin 20 at the surface of the solid supports 12, one example of which is described in reference to FIG. 1B. Other examples of library preparation may be used (e.g., including PCR), as long as the fragments are denatured into single stranded fragments before being hybridized to the oligonucleotides bound on the solid support 12 via biotin 20.

The library fragments 14, 14', 14" attached to the solid support 12 (in this example, the complexes 10A, 10B) may be added to a fluid. The fluid may be any aqueous buffer solution (e.g., a weak acid and one of its salts (conjugate base) or a weak base and one of its salts (conjugate acid). The salt concentration in the aqueous buffer solution may be adjusted so that the complexes 10A, 10B can flow to a desirable sequencing surface. The greater the density difference is between the solid support 12 and the fluid, the faster the settling time is of the complexes 10A, 10B. As examples, the fluid may be a Tris-HCl buffer or 0.5× saline sodium citrate (SSC) buffer.

The fluid containing the complexes 10A, 10B may then be introduced into the flow cell 24. Once introduced into the flow cell 24, the complexes 10A, 10B can become attached to the capture sites 44, 44' because the complexes 10A, 10B and the capture sites 44, 44' each include a member of a binding pair. In some examples, the binding pair is biotin-streptavidin. The capture sites 44 and/or 44' immobilize at least some of the complexes 10A, 10B.

It is to be understood that some complexes 10A, 10B in the fluid may not become captured, and these complexes 10A, 10B will be removed from the flow cell 24 before further processing. A predetermined time may be allowed to pass before removing the fluid and any non-immobilized complexes 10A, 10B from the flow cell 24. In an example, the predetermined time may range from about 5 minutes to about 30 minutes in order to obtain a desirable number of immobilized complexes 10A, 10B. Longer incubation times may also be used.

This example method then includes washing away the fluid and non-trapped complexes 10A, 10B from the flow cell 24. Washing may involve introducing a washing fluid into the flow cell 24. The flow may push any complexes 10A, 10B (or other target materials) that have not settled and become immobilized at the sequencing surface 30, 30' or 32, 32' out through an exit port of the flow cell 24. The immobilization mechanism (e.g., binding pair, hybridization, covalent bonding, etc.) between the complexes 10A, 10B (or other target materials) and the capture sites 44, 44' of the sequencing surface 30, 30' or 32, 32' may prevent any settled and immobilized complexes 10A, 10B (or other target materials) from becoming part of the exit flow.

The method involves introducing the first example of the cleavage composition into the flow cell 24. Any example of the first example of the cleavage composition disclosed herein may be used.

The first example of the cleavage composition is allowed to incubate in the flow cell 24 at a temperature ranging from about 60° C. to about 70° C. In one example, the temperature is about 65° C. In an example, the first example of the cleavage composition is allowed to incubate in the flow cell 24 for a time ranging from about 2 minutes to about 5 minutes. In one example, the time is about 5 minutes.

During incubation, the first example of the cleavage composition efficiently breaks the biotin-streptavidin bond that holds the library fragments 14, 14', 14" to the solid supports 12. As such, the first example of the cleavage composition causes at least some of the library fragments 14, 14', 14" to release from the solid supports 12. At the incubation temperatures, the released library fragments 14, 14', 14" are also able to seed to amplification primers 42, 42' on the sequencing surface(s) 30, 30' or 32, 32' of the flow cell 24. As such, library fragment 14, 14', 14" release and seeding may be accomplished in a single reagent.

The primers 42, 42' of the respective sequencing surface(s) 30, 30' or 32, 32' of the flow cell 24 can seed the released fragments 14, 14', or 14". Seeding is accomplished through hybridization between the first or second sequence of the adapter 18 or 22 of the fragment 14, 14', or 14" and a complementary one of the primers 42, 42' of the respective sequencing surface(s) 30, 30' or 32, 32'. Seeding may be performed at cleavage composition incubation temperature.

The location at which the 14, 14', or 14" seed within the flow cell 24 depends, in part, upon how the primers 42, 42' are attached. In examples of the flow cell 24 having the non-patterned sequencing surface(s) 30, 30', the released sequencing-ready nucleic acid fragments 14, 14', or 14" will seed across polymeric hydrogels 40, 40' in the concave regions 38, 38'. In examples of the flow cell 24 having the patterned sequencing surface(s) 32, 32', the released sequencing-ready nucleic acid fragments 14, 14', or 14" will seed across polymeric hydrogels 40, 40' within each of the depressions 48, 48'.

When the biotin-streptavidin binding pair is also used capture the complexes 10A, 10B to the capture sites 44, 44', the first example of the cleavage composition can also release the solid supports 12 from the capture sites 44, 44'.

As such, in some examples of the method at least some of the streptavidin coated solid supports 12 become bound to biotin capture sites 44, 44' on a surface of the flow cell 24; and the allowing of the biotin-streptavidin cleavage composition (the first examples of the cleavage composition) to incubate in the flow cell 24 also causes at least some of the bound streptavidin coated solid supports 12 to release from the biotin capture sites 44, 44'. Removal of the solid supports 12 after the fragments 14, 14', 14" are seeded is desirable for a clean surface for downstream clustering and sequencing.

When a different binding pair is used to capture the complexes 10A, 10B to the capture sites 44, 44', a separate release composition may be introduced into the flow cell 24 to remove the solid supports 12 from the capture sites 44, 44'.

This example method may then include rinsing the biotin-streptavidin cleavage composition (the first examples of the cleavage composition) from the flow cell 24 after incubation, thereby removing the streptavidin coated solid supports 12 and any unseeded library fragments 14, 14', 14". The flow may push any released solid supports 12 and any unseeded library fragments 14, 14', 14" out through an exit port of the flow cell 24. The immobilization mechanism (e.g., hybridization) between the fragments 14, 14', 14" and the amplification primers 42, 42' of the sequencing surfaces 30, 30' or 32, 32' may prevent any fragments 14, 14', 14" from becoming part of the exit flow.

A kit to perform this example of the method described herein may include a streptavidin coated solid support; an adapter sequence having biotin attached at one end, wherein the biotin is to be attached to the streptavidin coated solid support; a sample fluid including a genomic sequence that is to be fragmented and attached to the adapter sequence; and a biotin-streptavidin cleavage composition (the first examples of the cleavage composition), including from about 10% by volume to about 50% by volume of a formamide reagent and a balance of a salt buffer. The kit may also include other library preparation components, such as partial Y-adapters, transposase enzymes, etc.; each of which may be contained in a separate fluid until it is desirable to form any example complex 10A, 10B, etc. Some examples of the kit may also include the flow cell 24.

Method and Kit Involving Target Materials with Desthiobiotinylated-Streptavidin Bonds An example of the method that utilizes the second example of the cleavage composition generally includes introducing desthiobiotinylated library fragments to a flow cell 24, wherein the desthiobiotinylated library fragments are attached to streptavidin coated solid supports 12; introducing a cleavage composition to the flow cell 24, wherein the cleavage composition is at a temperature ranging from about 18° C. to about 30° C. and wherein the cleavage composition includes free biotin and a salt buffer; and increasing the temperature of the cleavage composition to about 60° C. to about 70° C., thereby causing at least some of the library fragments 14, 14', 14" to release from the solid supports 12 and to seed to amplification primers 42, 42' on a surface of the flow cell 24.

Prior to performing this example method, the library fragments 14, 14', 14" may be prepared and attached to the solid support 12 as described herein in reference to FIG. 1A or FIG. 1B.

The library fragments 14, 14', 14" attached to the solid support 12 (i.e., the complexes 10A, 10B in this example) may be added to a fluid. The fluid may be any aqueous buffer solution (e.g., a weak acid and one of its salts (conjugate base) or a weak base and one of its salts (conjugate acid).

The fluid containing the complexes 10A, 10B may be introduced into the flow cell 24. Once introduced into the flow cell 24, the complexes 10A, 10B can become attached to the capture sites 44, 44' because the complexes 10A, 10B and the capture sites 44, 44' each include a member of a binding pair. In some examples, the binding pair is desthiobiotin-streptavidin. The capture sites 44 and/or 44' immobilize at least some of the complexes 10A, 10B.

It is to be understood that some complexes 10A, 10B in the fluid may not become captured, and these complexes 10A, 10B will be removed from the flow cell 24 before further processing. A predetermined time may be allowed to pass before removing the fluid and any non-immobilized complexes 10A, 10B from the flow cell 24. In an example, the predetermined time may range from about 5 minutes to about 30 minutes in order to obtain a desirable number of immobilized complexes 10A, 10B. Longer incubation times may also be used.

This example method then includes washing away the fluid and non-trapped complexes 10A, 10B from the flow cell 24. Washing may involve introducing a washing fluid into the flow cell 24. The flow may push any complexes 10A, 10B that have not settled and become immobilized at the sequencing surface 30, 30' or 32, 32' out through an exit port of the flow cell 24. The immobilization mechanism between the complexes 10A, 10B (or other target materials) and the capture sites 44, 44' of the sequencing surface 30, 30' or 32, 32' may prevent any settled and immobilized complexes 10A, 10B from becoming part of the exit flow.

The method involves introducing the second example of the cleavage composition into the flow cell 24. Any example of the second example of the cleavage composition disclosed herein may be used.

The second example of the cleavage composition is introduced at a temperature ranging from about 18° C. to about 30° C. At this temperature and in the presence of the salt in the second example of the cleavage composition, the desthiobiotin is stabilized and its dissociation from the solid support 12 is reduced or prevented even though the free biotin is also present. The introduced cleavage composition is allowed to settle so that fluid flow and/or mixing at least substantially ceases.

The temperature of the cleavage composition is then increased to a temperature ranging from about 60° C. to about 70° C. In one example, the temperature of the cleavage composition is raised to about 65° C. At this temperature and in the presence of the free biotin, the desthiobiotin is destabilized and dissociates from the solid support 12. This releases the library fragments 14, 14', 14". At these temperatures, the released library fragments 14, 14', 14" are also able to seed to amplification primers 42, 42' on the sequencing surface(s) 30, 30' or 32, 32' of the flow cell 24. Because fluid flow and/or mixing is not taking place when the library fragments 14, 14', 14" are released, the released library fragments 14, 14', 14" are able to diffuse and seed on the flow cell surface at or near the solid support 12 from which they are released. As such, library fragment 14, 14', 14" release and diffusion-dependent spatial seeding may be accomplished in a single reagent.

When the desthiobiotin-streptavidin binding pair is also used capture the complexes 10A, 10B to the capture sites 44, 44', the second example of the cleavage composition can also release the solid supports 12 from the capture sites 44, 44'.

As such, in some examples of the method, at least some of the streptavidin coated solid supports 12 become bound to desthiobiotin capture sites 44, 44' on a surface of the flow cell 24; and raising the temperature of the already introduced desthiobiotin-streptavidin cleavage composition (the second example of the cleavage composition) causes at least some of the bound streptavidin coated solid supports 12 to release from the desthiobiotin capture sites 44, 44'. Removal of the solid supports 12 after the fragments 14, 14', 14" are seeded is desirable for a clean surface for downstream clustering and sequencing.

When a different binding pair is used to capture the complexes 10A, 10B to the capture sites 44, 44', a separate release composition may be introduced into the flow cell 24 to remove the solid supports 12 from the capture sites 44, 44'.

This example method may then include rinsing the desthiobiotin-streptavidin cleavage composition (the second example of the cleavage composition) from the flow cell 24 after seeding, thereby removing the streptavidin coated solid supports 12 and any unseeded library fragments 14, 14', 14". The flow may push any released solid supports 12 and any unseeded library fragments 14, 14', 14" out through an exit port of the flow cell 24. The immobilization mechanism (e.g., hybridization) between the fragments 14, 14', 14" and the amplification primers 42, 42' of the sequencing surfaces 30, 30' or 32, 32' may prevent any fragments 14, 14', 14" from becoming part of the exit flow.

A kit to perform this example of the method described herein may include a streptavidin coated solid support 12; an adapter sequence having desthiobiotin attached at one end, wherein the desthiobiotin is to be attached to the streptavidin coated solid support; a sample fluid including a genomic sequence that is to be fragmented and attached to the adapter sequence; and a desthiobiotin-streptavidin cleavage composition (the second example of the cleavage composition) including free biotin and a salt buffer. The kit may also include other library preparation components, such as partial Y-adapters, transposase enzymes, etc.; each of which may be contained in a separate fluid until it is desirable to form any example complex 10A, 10B, etc. Some examples of the kit may also include the flow cell 24.

Method and Kit Involving Two-Step Release

As mentioned, some examples disclosed herein utilize the dual release mechanism for releasing the sequencing-ready library fragments 14, 14' from the library preparation beads 11. The dual release mechanism utilizes the cleavage site 64 and the splint 68. As will be described in more detail with reference to FIG. 4, a suitable cleaving agent may be used to remove the cleavage site 64, and heat may be used to remove the splint 68. Because the cleavage conditions involve two orthogonal processes (where one process does not initiate, affect, or otherwise interfere with the other process), this example allows for controlled release of the library fragments 14, 14'.

The dual mechanism release may take place on the sequencing surface 30, 30' or 32, 32' of the flow cell 24, or may take place in another reaction vessel, such as a test tube.

This example method is schematically shown in FIG. 4 and generally includes introducing a plurality of prepped library preparation beads 11' to a reaction vessel (not shown), each of the prepped library preparation beads 11' including a solid support 12; a plurality of bridged molecules 72, 72' attached to the solid support 12, each of the bridged molecules 72, 72' including: a double stranded DNA fragment 16 and 16'; a transferred strand 58, 58' respectively attached to each strand 16, 16' of the double stranded DNA fragment at its 5' end, each transferred strand 58, 58' including a 3' transposon end sequence 62A, 62A', a first adapter sequence 18, 18', a cleavage site 64, 64', and a 5' linking end sequence 66, 66', wherein the first adapter sequence 18, 18' and the 5' linking end sequence 66, 66' flank the cleavage site 64, 64'; and a second adapter 22, 22' respectively attached to each strand 16, 16' of the double stranded DNA fragment at its 3' end; and a splint sequence 68, 68' hybridized to at least a portion of the first adapter sequence 18, 18' and at least a portion of the 5' linking sequence 66, 66' such that it splints the cleavage site 64, 64'; exposing the prepped library preparation beads 11' to a cleaving agent 74 to remove the cleavage site 64, 64', whereby the plurality of bridged molecules 72, 72' remains attached to the solid support 12 through the splint 68, 68'; and heating the reaction vessel to a dissociation temperature of the splint 68, 68' and the double stranded DNA fragment 16, 16'.

The prepped library preparation beads 11' are shown at the left side if FIG. 4. The prepped library preparation beads 11' may be prepared using the method described in reference to FIG. 2A through FIG. 2C. As such, each of the bridged molecules 72, 72' includes the sequencing-ready nucleic acid fragments 14, 14' (which includes the fragments 16, 16', the 3' transposon end sequence 62A, 62A' near the 5' end, and the respective adapters 18, 22 or 18', 22" at the opposed ends), as well as the cleavage site 64, 64', the 5' linking end sequence 66, 66', and the splint 68, 68'.

While a single set of bridged molecules 72, 72' is shown on the solid support 12 in FIG. 4, it is to be understood that a single solid support 12 may include several sets of bridged molecules 72, 72'.

To initiate release of the sequencing-ready nucleic acid fragments 14, 14' from the bridged molecules 72, 72' and solid support 12, the method first involves exposing the prepped library preparation beads 11' to a cleaving agent 74. The cleaving agent 74 that is used will depend upon the cleavage site 64, 64' of the transferred strand 58, 58'. When the cleavage site 64, 64' is a chemical cleavage site, exposing the prepped library preparation beads 11' to the cleaving agent 74 involves introducing a chemical cleaving agent to the reaction vessel. As one example, periodate may be used to cleave a 1,2-diol chemical cleavage site. When the cleavage site 64, 64' is an enzymatic cleavage site, exposing the prepped library preparation beads 11' to the cleaving agent involves introducing an enzymatic cleaving agent to the reaction vessel. As examples, the USER enzyme may be used to cleave deoxyuracil nucleotides, and RNase may be used to cleave a ribonucleotide. When the cleavage site 64, 64' is a photocleavable cleavage site, exposing the prepped library preparation beads 11' to the cleaving agent 74 involves irradiating the reaction vessel with light of a wavelength that activates cleavage. As an example, a nitrobenzyl linker may be exposed to 365 nm ultraviolet light.

The incubation of the chemical or enzymatic cleaving agent or the light exposure may take place for a time sufficient to cleave the cleavage site 64, 64'. The incubation time may depend, in part, upon the reactivity of the chemical or enzymatic cleaving agent, and the light exposure time may depend upon the light source (e.g., its intensity). In one example, the incubation time ranges from 30 minutes to about 3 hours. In another example, the light exposure may range from about 30 seconds to about 2 minutes. The chemical or enzymatic cleaving agent may then be removed from the reaction vessel or the light irradiation may be stopped. The prepped library preparation beads 11' may then be washed (e.g., with water, buffer, etc.) to remove the cleaved cleavage sites 64, 64', and, in some instances, the chemical or enzymatic cleaving agent.

As shown in the center of FIG. 4, after cleavage of the cleavage site 64, 64', the sequencing-ready fragments 14, 14' remain attached to the solid support 12. The splint 68, 68' is not susceptible to the cleaving agent 74, and thus the sequencing-ready fragments 14, 14' remain bridged and attached to the solid support 12.

To complete the release of the sequencing-ready nucleic acid fragments 14, 14' from the bridged molecules 72, 72' and the solid support 12, the method then involves exposing the prepped library preparation beads 11' to heat. The temperature selected is capable of dissociating the splint 68, 68' from the adapter 18, 18' and the 5' linking end sequence 66, 66', as well as dissociating any double stranded portions of the sequencing-ready fragments 14, 14'. In an example, the temperature for heating ranges from about 60° C. to about 70° C.

When the dual mechanism release of the sequencing-ready library fragments 14, 14' from the prepped library preparation beads 11' occurs on a flow cell 24, at least some of the plurality of prepped library preparation beads 11' become immobilized on the surface of the flow cell 24 (e.g., via capture sites 44, 44' when introduced into the flow cell 24); and the method further comprises removing non-immobilized library preparation beads 11' from the flow cell prior to exposing the prepped library preparation beads 11' to the cleaving agent 74.

Additionally, when the dual mechanism release of the sequencing-ready library fragments 14, 14' from the prepped library preparation beads 11' occurs on a flow cell 24, spatial release of the fragments 14, 14' is achieved. Because the final release mechanism is heat, fluid flow and/or inertial mixing are absent or minimally present, and thus the released fragments 14, 14' can seed to primers 42, 42' that are within proximity of the solid support 12 from which the fragments 14, 14' are released.

Sequencing

When the fragment 14, 14', 14" release takes place on the flow cell 24, the fragments 14, 14', 14" may seed to the primers 42, 42' on the flow cell sequencing surface(s) 30, 30' or 32, 32'. When the fragment 14, 14', 14" release takes place in another reaction vessel, the released fragments 14, 14', 14" may be separated from the solid supports 12 (having the 5' linking end sequence 66 attached thereto as shown at the right hand side of FIG. 4) and the library fragments 14, 14', 14" may be introduced to a flow cell 24 for seeding to the primers 42, 42'.

With the fragments 14, 14', 14" released and seeded, the flow cell 24 is ready for downstream analysis.

The seeded library fragments 14, 14', 14" can be amplified using cluster generation.

In one example of cluster generation, the fragments 14, 14', or 14" are copied from the hybridized primers 42, 42' by 3' extension using a high-fidelity DNA polymerase. The original fragments 14, 14', or 14" are denatured, leaving the copies immobilized to the sequencing surface(s) 30, 30' or 32, 32'. Isothermal bridge amplification or some other form of amplification may be used to amplify the immobilized copies. For example, the copied templates loop over to hybridize to an adjacent, complementary primer 42, 42', and a polymerase copies the copied templates to form double stranded bridges, which are denatured to form two single stranded strands. These two strands loop over and hybridize to adjacent, complementary primers 42, 42' and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. Clustering results in the formation of several template polynucleotide strands along the sequencing surface(s) 30, 30' or 32, 32'. This example of clustering is bridge amplification, and is one example of the amplification that may be performed. It is to be understood that other amplification techniques may be used, such as the exclusion amplification (Examp) workflow (Illumina Inc.).

A sequencing primer may be introduced that hybridizes to a complementary sequence on the template polynucleotide strand. This sequencing primer renders the template polynucleotide strand ready for sequencing. The 3'-ends of the templates and any flow cell-bound primers 20 (not attached to the copy) may be blocked to prevent interference with the sequencing reaction, and in particular, to prevent undesirable priming.

To initiate sequencing, an incorporation mix may be added to the flow cell 24. In one example, the incorporation mix includes a liquid carrier, a polymerase, and fluorescently labeled nucleotides. The fluorescently labeled nucleotides may include a 3' OH blocking group. When the incorporation mix is introduced into the flow cell 24, the fluid enters the flow channel 28, and in some examples, into the depressions 48, 48' (where the template polynucleotide strands are present).

The fluorescently labeled nucleotides are added to the sequencing primer (thereby extending the sequencing primer) in a template dependent fashion such that detection of the order and type of nucleotides added to the sequencing primer can be used to determine the sequence of the template. More particularly, one of the nucleotides is incorporated, by a respective polymerase, into a nascent strand that extends the sequencing primer and that is complementary to the template polynucleotide strand. In other words, in at least some of the template polynucleotide strands across the flow cell 24, respective polymerases extend the hybridized sequencing primer by one of the nucleotides in the incorporation mix.

The incorporation of the nucleotides can be detected through an imaging event. During an imaging event, an illumination system (not shown) may provide an excitation light to the respective sequencing surface(s) 30, 30' or 32, 32'.

In some examples, the nucleotides can further include a reversible termination property (e.g., the 3' OH blocking group) that terminates further primer extension once a nucleotide has been added to the sequencing primer. For example, a nucleotide analog having a reversible terminator moiety can be added to the sequencing primer such that subsequent extension cannot occur until a deblocking agent is delivered to remove the moiety. Thus, for examples that use reversible termination, a deblocking reagent can be delivered to the flow cell 24 after detection occurs.

Wash(es) may take place between the various fluid delivery steps. The SBS cycle can then be repeated n times to extend the sequencing primer by n nucleotides, thereby detecting a sequence of length n.

In some examples, the forward strands may be sequenced and removed, and then reverse strands are constructed and sequenced as described herein.

While SBS has been described in detail, it is to be understood that the flow cells 24 described herein may be utilized with other sequencing protocol, for genotyping, or in other chemical and/or biological applications. In some instances, the primers 42, 42' of the flow cell 24 may be selected to enable simultaneous paired-end sequencing, where both forward and reverse strands are present on the polymeric hydrogel 40, 40', allowing for simultaneous base calling of each read. Sequential and simultaneously paired-end sequencing facilitates detection of genomic rearrangements and repetitive sequence elements, as well as gene fusions and novel transcripts. In another example, the flow cells 24 disclosed herein may be used for on-cell library generation.

To further illustrate the present disclosure, examples are given herein. It is to be understood that these examples are provided for illustrative purposes and are not to be construed as limiting the scope of the present disclosure.

NON-LIMITING WORKING EXAMPLES

Example 1

Complexes similar to those shown in FIG. 1A were prepared having an average diameter of 3 µm. The solid supports of the complexes were DYNABEADS™ M-280 Streptavidin beads from ThermoFisher Scientific. The fragments on a particular bead were from the same long DNA molecule (from the Human genome). The library fragments were attached to the solid support via a biotin oligo. The library fragments included P5' and P7 sequences, along with index sequences, and read 1 and read 2 sequences.

The complexes were incorporated into a saline sodium citrate buffer with sodium dodecyl sulfate, and this fluid was loaded into a flow cell including a non-patterned sequencing surface (including P5 and P7 primers) and a lid. The non-patterned sequencing surface also included biotin capture sites.

The flow cell was then washed with a washing solution.

A first example of the cleavage composition disclosed herein was prepared including about 40% by volume a formamide reagent including formamide and trisodium citrate and about 60% by volume of a salt buffer including sodium chloride, sodium citrate, and a biocompatible surfactant. The cleavage solution was introduced into the flow cell and allowed to incubate at 80° C. for about 20 seconds. The flow cell was then cooled to 20° C. and was maintained at that temperature for about 3 minutes.

The flow cell was then washed with a washing solution to remove solid supports and any unseeded released library fragments.

The released and seeded library fragments were grown to clusters with cycle amplification. The clusters are then stained with Sytox green. The resulting image (not reproduced herein) indicated that the library fragments seeded and were amplified near the complexes.

Sequencing was then performed on the flow cell. The sequencing results showed that the long DNA molecular coverage was close to 40%. This indicated that the first example of the cleavage composition disclosed herein resulted in efficient release of the library fragments from the solid supports.

Example 2

Several different cleavage compositions according to the first example disclosed herein were prepared including a formamide reagent (including formamide and trisodium citrate) and a salt buffer (including sodium chloride, sodium citrate, and a biocompatible surfactant). The percentages of the reagent and buffer in each cleavage composition are shown in Table 1.

TABLE 1

| Sample | Formamide reagent (vol %) | Salt Buffer (vol %) |
| --- | --- | --- |
| CC 1 (comparative example) | 0 | 100 |
| CC 2 | 10 | 90 |
| CC 3 | 20 | 80 |
| CC 4 | 30 | 70 |
| CC 5 | 40 | 60 |
| CC 6 (comparative example) | 50 | 50 |
| CC 7 (comparative example) | 60 | 40 |
| CC 8 (comparative example) | 70 | 30 |

Figure 5:
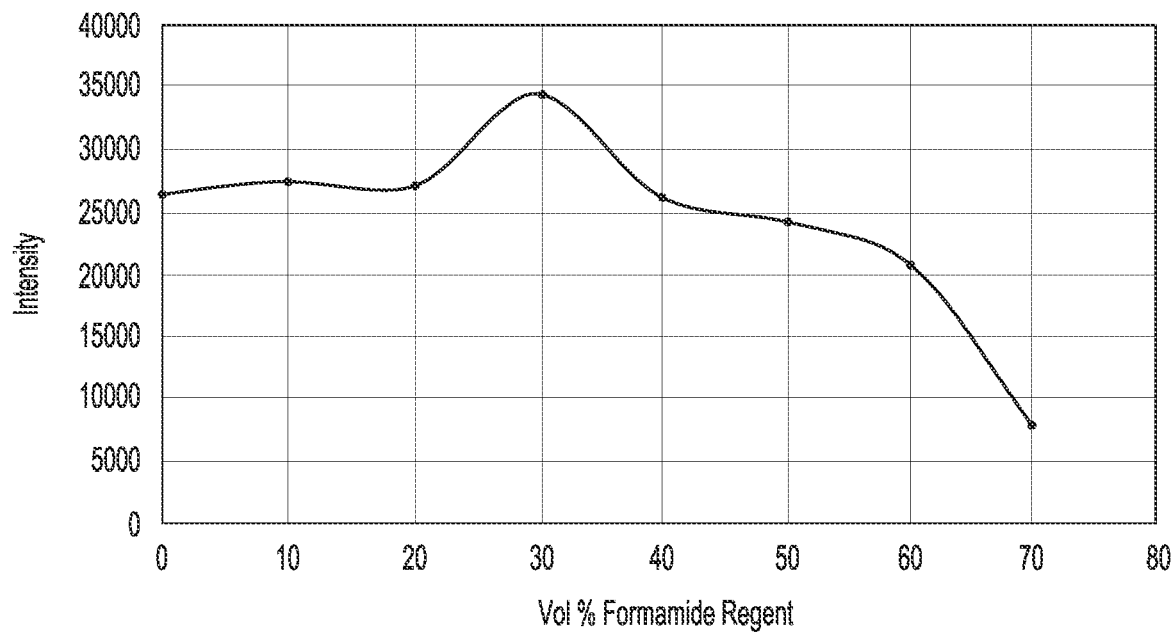
FIG. 5 is a graph depicting the fluorescence intensity of a tetrachloro-fluorescein (TET) QC primer (Y-axis) relative to the volume % of formamide reagent in a cleavage composition (X-axis)

Flow cell surface P5 and P7 primers were hybridized to TET QC primers (e.g., complementary P5 and P7 (cP5 and cP7) primers labeled with a fluorescent dye). In this example, the fluorescent label was used as a reporter of a denaturing event. If the reagent caused denaturing, then the fluorescent labeled primers leave the surface and lower fluorescent intensity resulted. The TET intensity (fluorescence) versus the percentage of formamide reagent used in the cleavage composition is shown in FIG. 5. As depicted, when the formamide reagent was increased to 60% by volume, the fluorescent signal decreased. This indicated that the seeded library fragments were denaturing. When the formamide reagent was increased to 70% by volume, the biotin-streptavidin bond could be cleaved, but it was found that the hybridization of the surface P5/P7 primers was not stable, even at room temperature. As such, the volume ratio of formamide reagent:salt buffer in the examples disclosed ranges from 1:9 to about 1:1 to ensure both bond cleavage and desirable seeding conditions.

Example 3

DYNABEADS™ M-280 Streptavidin beads from ThermoFisher Scientific were incorporated into a saline sodium citrate buffer with sodium dodecyl sulfate, and this fluid was loaded into a flow cell including a non-patterned sequencing surface (including P5 and P7 primers) and a lid. The non-patterned sequencing surface also included biotin capture sites. Therefore, the M-280 beads were immobilized on the surface via biotin-streptavidin bonding.

The non-patterned sequencing surface was imaged and the immobilized beads on the surface were counted using microscope images.

The flow cell was then washed with a comparative cleavage agent (a formamide reagent including formamide and trisodium citrate). The comparative cleavage agent was allowed to incubate for 2 minutes at 65° C. The non-patterned sequencing surface was imaged and the immobilized beads on the surface were counted using microscope images.

The flow cell was then washed with a first example of the cleavage composition disclosed herein (referred to as the example cleavage agent), including about 50% by volume a formamide reagent including formamide and trisodium citrate and about 50% by volume of a salt buffer including sodium chloride, sodium citrate, and a biocompatible surfactant. The example cleavage agent was allowed to incubate for 2 minutes at 65° C. The non-patterned sequencing surface was imaged and the immobilized beads on the surface were counted using microscope images.

The flow cell was again washed with the example cleavage agent, and was imaged. The example cleavage agent was again allowed to incubate for 2 minutes at 65° C. After the second wash with the example cleavage agent, the immobilized beads on the surface were counted using microscope images.

Figure 6:
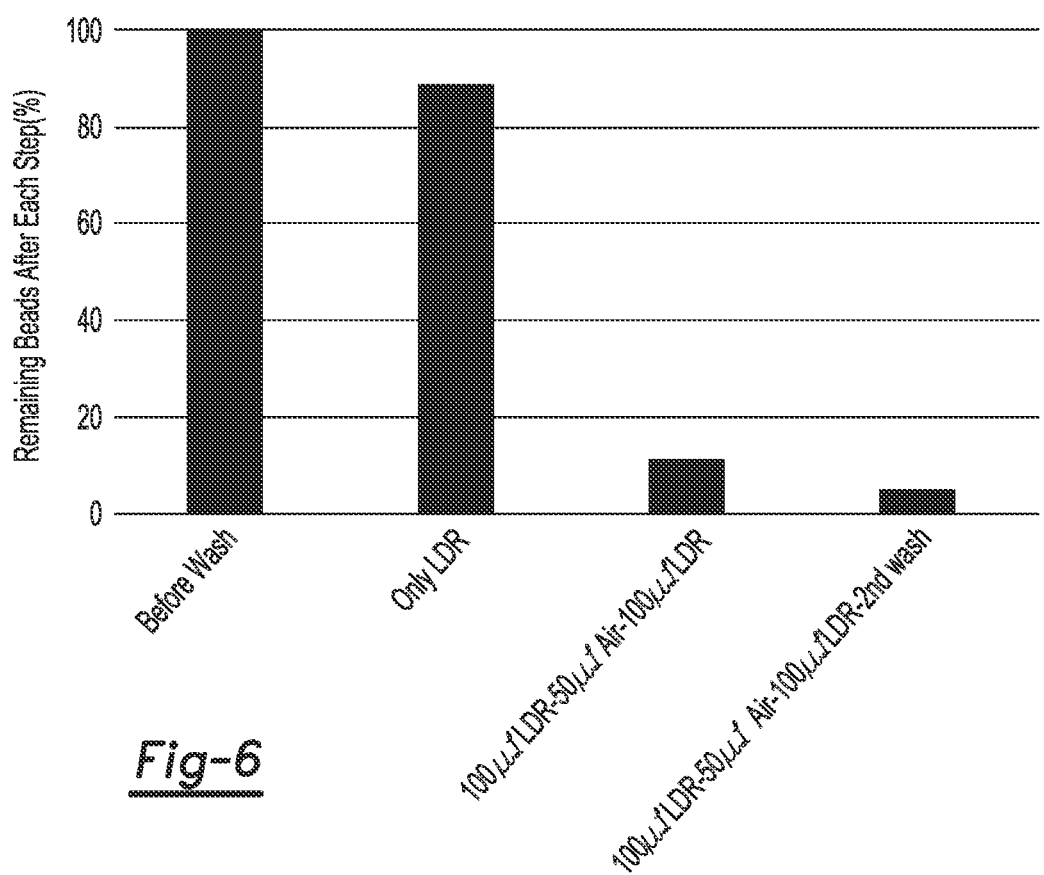
FIG. 6 is a bar graph depicting the percentage of beads remaining after various washing steps.

The number of beads that were counted on the flow cell surface before wash, after washing with the comparative cleavage agent, after the first wash with the example cleavage agent, and after the second wash with the example cleavage agent are shown in FIG. 6.

Pre-wash, 100% of the beads in the solution had immobilized on the flow cell surface. After washing with the comparative cleavage agent, less than 15% of the beads were removed. After the first washing with the example cleavage agent, about 85% of the beads were removed. After the second washing with the example cleavage agent, about 90% of the beads were removed. These results illustrate that the example cleavage mix disclosed herein is effective at breaking the streptavidin-biotin bond.

Example 4

DNA fragments were attached to DYNABEADS™ M-280 Streptavidin beads from ThermoFisher Scientific using desthiobiotin. The thermal release of the desthiobiotinylated DNA was tested at different temperatures and in different conditions (e.g., in the presence of free biotin or free desthiobiotin).

Mixtures of free biotin and free desthiobiotin were prepared in 825 mM sodium salt aqueous solutions. The first mixture contained 100 µM desthiobiotin, the second mixture contained 2.5 µM biotin, and the third mixture contained 10 µM biotin.

Control samples were exposed to either 25° C. or 60° C. without any of the mixtures. Example samples were exposed to either 25° C. or 60° C. in the presence of the first mixture (100 µM desthiobiotin), the second mixture (2.5 µM biotin), or the third mixture (10 µM biotin). The percentage of DNA released from the beads after the respective treatments was determined by quantitative PCR. The results are shown in FIG. 7.

Figure 7:
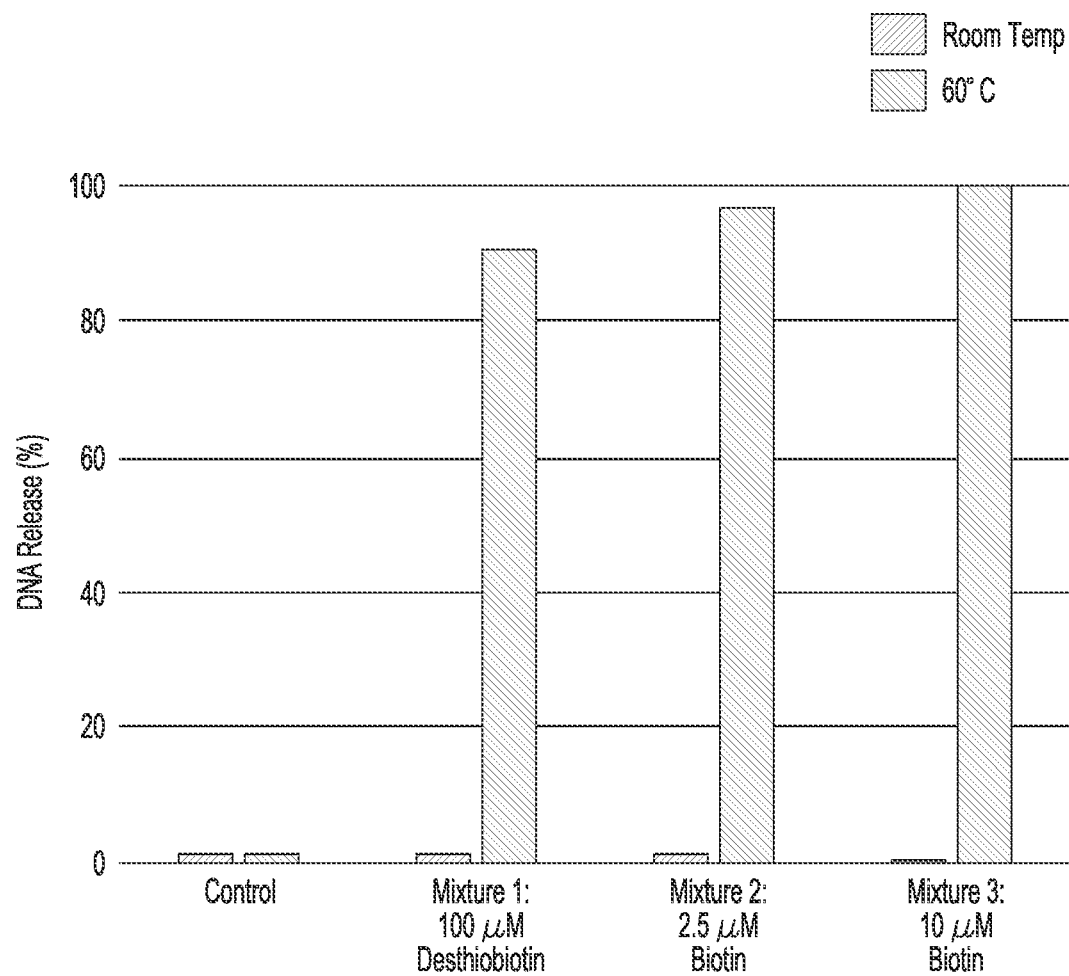
FIG. 7 is a bar graph depicting the percentage of desthiobiotinylated DNA release at different temperatures and when exposed to free biotin or desthiobiotin under high salt conditions.

As depicted in FIG. 7, almost none of the desthiobiotinylated DNA fragments were released from the beads in the absence of free biotin or free desthiobiotin at either 25° C. or 60° C. (the control). Similarly, almost none of the desthiobiotinylated DNA fragments were released from the beads in the presence of free desthiobiotin or free biotin (regardless of concentration) at 25° C. The beads exposed to third mixture (10 µM free biotin) at 25° C. exhibited the lowest DNA fragment release, with only about 1.5% of the desthiobiotinylated DNA fragments being released. In contrast, about 90% of the desthiobiotinylated DNA fragments were released from the beads in the presence of free desthiobiotin at 60° C. (mixture 1), and over 95% of the desthiobiotinylated DNA fragments were released from the beads in the presence of free biotin (regardless of concentration, see results for mixtures 2 and 3) at 60° C. Higher DNA fragment release was observed in the presence of free biotin at 60° C. at much lower concentrations than in the presence of free biotin at 25° C.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

While several examples have been described in detail, it is to be understood that the disclosed examples may be modified. Therefore, the foregoing description is to be considered non-limiting.

What is claimed is:

1. A method, comprising:
   introducing library fragments to a flow cell, wherein the library fragments are attached to streptavidin coated solid supports;
   introducing a biotin-streptavidin cleavage composition to the flow cell, the biotin-streptavidin cleavage composition including:
      from about 10% by volume to about 50% by volume of a formamide reagent, the formamide reagent including 100% formamide or a combination of formamide and a buffer; and
      a balance of a salt buffer; and
   allowing the biotin-streptavidin cleavage composition to incubate in the flow cell at a temperature ranging from about 60° C. to about 70° C., thereby causing at least some of the library fragments to release from the solid supports and to seed to amplification primers on a surface of the flow cell.

2. The method as defined in claim 1, wherein the biotin-streptavidin cleavage composition is allowed to incubate in the flow cell for a time ranging from about 2 minutes to about 5 minutes.

3. The method as defined in claim 1, wherein:
   at least some of the streptavidin coated solid supports become bound to biotin capture sites on a surface of the flow cell; and
   the allowing of the biotin-streptavidin cleavage composition to incubate in the flow cell also causes at least some of the bound streptavidin coated solid supports to release from the biotin capture sites.

4. The method as defined in claim 3, further comprising rinsing the biotin-streptavidin cleavage composition from the flow cell after incubation, thereby removing the streptavidin coated solid supports and any unseeded library fragments.

5. The method as defined in claim 1, further comprising preparing the biotin-streptavidin cleavage composition by mixing the formamide reagent and the salt buffer.

6. The method as defined in claim 5, wherein the salt buffer includes about 0.75 M sodium chloride and about 75 mM sodium citrate in water.

7. The method as defined in claim 5, wherein the salt buffer further includes from about 0.25 wt % to about 1.5 wt % of a biocompatible surfactant.

8. A method, comprising:
   introducing desthiobiotinylated library fragments to a flow cell, wherein the desthiobiotinylated library fragments are attached to streptavidin coated solid supports;
   introducing a cleavage composition to the flow cell, wherein the cleavage composition is at a temperature ranging from about 18° C. to about 30° C. and wherein the cleavage composition includes:
      free biotin; and
      a salt buffer; and
   increasing the temperature of the cleavage composition to about 60° C. to about 70° C., thereby causing at least some of the library fragments to release from the solid supports and to seed to amplification primers on a surface of the flow cell.

9. The method as defined in claim 8, wherein the salt buffer includes from about 0.75 M salt to about 0.85 M salt in water.

10. The method as defined in claim 8, wherein the free biotin is present in the cleavage composition at a concentration ranging from about 2.5 µM to about 10 mM.

11. The method as defined in claim 8 wherein the salt buffer includes about 0.75 M sodium chloride and about 75 mM sodium citrate in water.

\* \* \* \* \*